(12) United States Patent
Rowland et al.

(10) Patent No.: US 11,672,925 B2
(45) Date of Patent: Jun. 13, 2023

(54) INHALER DEVICE FOR INHALABLE LIQUIDS

(71) Applicant: Medical Developments International Limited, Scoresby (AU)

(72) Inventors: Greg Rowland, Scoresby (AU); Edward Linacre, Abbotsford (AU); Glenn Gilbert, Scoresby (AU); Viktor Legin, Abbotsford (AU)

(73) Assignee: MEDICAL DEVELOPMENTS INTERNATIONAL LIMITED, Scoresby (AU)

( * ) Notice: Subject to any disclaimer, the term of this patent is extended or adjusted under 35 U.S.C. 154(b) by 359 days.

(21) Appl. No.: 17/029,451

(22) Filed: Sep. 23, 2020

(65) Prior Publication Data

US 2021/0001060 A1     Jan. 7, 2021

Related U.S. Application Data

(63) Continuation of application No. 15/745,876, filed as application No. PCT/AU2016/050636 on Jul. 19, 2016, now abandoned.

(30) Foreign Application Priority Data

Jul. 20, 2015   (AU) ................................ 2015902864
Jul. 20, 2015   (AU) ................................ 2015902881

(51) Int. Cl.
*A61M 15/00*   (2006.01)
*A61M 15/06*   (2006.01)
(Continued)

(52) U.S. Cl.
CPC ......... *A61M 15/002* (2014.02); *A61K 9/0073* (2013.01); *A61K 31/08* (2013.01);
(Continued)

(58) Field of Classification Search
CPC ...... A61M 11/00; A61M 11/04; A61M 15/00; A61M 15/0001; A61M 15/0013;
(Continued)

(56) References Cited

U.S. PATENT DOCUMENTS 363,067 A    5/1887   Heintzelitian
957,548 A    5/1910   Doane
(Continued)

FOREIGN PATENT DOCUMENTS

RU     2008117423 A    9/2006
RU       2383358 C2    3/2010
(Continued)

OTHER PUBLICATIONS

Robbins, B.H., "Preliminary studies of the anesthetic activity of fluorinated hydrocarbons", J Pharmacol Exp Ther, Feb. 1946; 86: pp. 197-204.
(Continued)

*Primary Examiner* — Joseph D. Boecker
(74) *Attorney, Agent, or Firm* — Westman, Champlin & Koehler, P.A.

(57) ABSTRACT

The present invention provides a new inhaler device for the storage and/or administration of inhalable liquids to a patient offering one or more advantages or improvements over known inhalers, particularly inhalers for the delivery of halogenated volatile liquids such as methoxyflurane for use as an analgesic.

20 Claims, 16 Drawing Sheets

(51) Int. Cl.
  *A61M 11/04* (2006.01)
  *A61M 16/01* (2006.01)
  *A61P 29/00* (2006.01)
  *A61K 9/00* (2006.01)
  *A61K 31/08* (2006.01)

(52) U.S. Cl.
  CPC ........ *A61M 11/04* (2013.01); *A61M 15/0013* (2014.02); *A61M 15/0018* (2014.02); *A61M 15/0021* (2014.02); *A61M 15/0035* (2014.02); *A61M 15/0086* (2013.01); *A61M 15/06* (2013.01); *A61P 29/00* (2018.01); *A61M 16/01* (2013.01); *A61M 2202/0241* (2013.01)

(58) Field of Classification Search
  CPC .......... A61M 15/0016; A61M 15/0018; A61M 15/002; A61M 15/0021; A61M 15/0035; A61M 15/0086; A61M 15/009; A61M 15/06; A61M 2202/0241; A24F 47/002; A24F 40/05
  See application file for complete search history.

(56) References Cited

U.S. PATENT DOCUMENTS

| | | | |
|---|---|---|---|
| 3,565,071 A | 2/1971 | Cobb et al. | |
| 4,725,442 A | 2/1988 | Haynes | |
| 9,205,206 B2 | 12/2015 | Hamaguchi et al. | |
| 2001/0013341 A1 | 8/2001 | Gallem | |
| 2007/0062548 A1 | 3/2007 | Horstmann et al. | |
| 2008/0023003 A1 | 1/2008 | Rosenthal | |
| 2010/0083963 A1* | 4/2010 | Wharton | A61M 15/009 128/203.15 |
| 2011/0290267 A1 | 12/2011 | Kamada et al. | |
| 2015/0237913 A1 | 8/2015 | Suzuki et al. | |
| 2015/0374938 A1 | 12/2015 | Scheiber et al. | |
| 2018/0200459 A1 | 7/2018 | Rowland et al. | |
| 2018/0207390 A1 | 7/2018 | Rowland et al. | |
| 2019/0209792 A1 | 7/2019 | Nicoll et al. | |
| 2021/0113803 A1* | 4/2021 | Rowland | A61M 16/142 |

FOREIGN PATENT DOCUMENTS

| | | | |
|---|---|---|---|
| WO | 1997003711 A2 | 2/1997 | |
| WO | 1999034762 A1 | 7/1999 | |
| WO | 2002022195 A2 | 3/2002 | |
| WO | 2002094360 A1 | 11/2002 | |
| WO | 2003032890 A1 | 4/2003 | |
| WO | 2007033400 A1 | 3/2007 | |
| WO | 2008036858 A2 | 3/2008 | |
| WO | 2008040062 A1 | 4/2008 | |
| WO | 2008070490 A2 | 6/2008 | |
| WO | 2009094459 A1 | 7/2009 | |
| WO | 2009094460 A2 | 7/2009 | |
| WO | 2009117529 A2 | 9/2009 | |
| WO | 2010017586 A1 | 2/2010 | |
| WO | WO-2010017586 A1 * | 2/2010 | .......... A61M 11/041 |
| WO | 2010025505 A1 | 3/2010 | |
| WO | 2010129686 A1 | 11/2010 | |
| WO | 2010129796 A1 | 11/2010 | |
| WO | 2010135436 A1 | 11/2010 | |
| WO | 2012116187 A1 | 8/2012 | |
| WO | 2013016511 A1 | 1/2013 | |
| WO | 2013106608 A1 | 7/2013 | |
| WO | 2013149263 A1 | 10/2013 | |
| WO | 2014143964 A2 | 9/2014 | |
| WO | 2015034978 A1 | 3/2015 | |
| WO | 2015121673 A1 | 8/2015 | |

OTHER PUBLICATIONS

Terrell, R.C., "The Invention and Development of Enflurane, Isoflurane, Sevoflurane, and Desflurane", Anesthesiology 2008; 108: pp. 531-533.

International Search Report and Written Opinion Issued in PCT Application No. PCT/AU2016/050636, dated Sep. 20, 2016.

Search Report issued in Russian Application RU2018106076, dated Oct. 23, 2019.

* cited by examiner

INHALER DEVICE FOR INHALABLE LIQUIDS

CROSS-REFERENCE TO RELATED APPLICATION(S)

The present application is a continuation of and claims priority to U.S. patent application Ser. No. 15/745,876, filed Jan. 18, 2018, which is a § 371 national phase entry of International patent application Serial No. PCT/AU2016/050636, filed Jul. 19, 2016, and published in English, and which claims priority to Australian Patent Application Nos. 2015902864 and 2015902881, both filed on Jul. 20, 2015, the content of each of which is hereby incorporated by reference in its entirety.

FIELD

The present invention relates to an inhaler device for inhalable liquids, in particular for the storage and/or administration of inhalable volatile liquids such as halogenated volatile liquids, to a patient.

BACKGROUND

The storage and administration of inhalable liquids to patients that comprise active agents, or that are themselves the active agent, commonly presents challenges. Due to patient preference and ease of self-administration or administration in a hospital setting or other settings as required, active agents such as therapeutic agents or pharmaceutical agents, are often formulated for oral delivery in the form of tablets and capsules, nasal delivery in the form of sprays and liquid formulations for intravenous delivery.

Where it is advantageous to administer active agents to a patient's lungs, for example to treat or alleviate respiratory diseases, the active agent may be administered by the oral inhalation route, alone or in combination with the intranasal route. Suitable inhaler devices may include, for example, metered dose inhalers and dry powder inhalers. These types of oral inhalation devices typically require pressurised means to deliver the active agent to the desired site of action in the lungs. In addition, liquids that contain active agents or that are themselves the active agent usually require transformation into an inhalable, respirational, form at the point of administration to be suitable for delivery by the inhalation route. Transforming a liquid into an inhalable form, such as by nebulisation or aerosolizing into respirational sized droplets or heating to form a vapor, requires delivery devices to include moving, mechanical, heating and/or electrical means which adds to the complexity of the design, manufacturing and end user costs, operability and/or patient use.

The use of volatile liquids as active agents or comprising active agents is known. One such example is halogenated volatile liquids. Halogenated volatile liquids have been described as useful for inducing and/or maintaining anaesthesia (including amnesia, muscle paralysis, and/or sedation) and/or analgesia and may therefore be useful as anaesthetics and/or analgesics. The anaesthetic properties of fluorinated compounds have been known since at least 1946 (Robbins, B. H. *J Pharmacol Exp Ther* (1946) 86: 197-204). This was followed by the introduction of fluoroxene, halothane and methoxyflurane into clinical use in the 1950s and the subsequent development of enflurane, isoflurane, sevoflurane and desflurane which are in clinical use in some countries today (Terrell, R. C. *Anesthesiology* (2008) 108 (3): 531-3).

Halogenated volatile liquids, when used for general anaesthesia, may be delivered to a patient under positive pressure via a delivery system that includes a vaporizer and a flow of breathable carrier gas. More recently, halogenated volatile liquids have been formulated for use in local or regional anaesthesia and delivery via non-inhalation routes. Examples include formulation as: microdroplets for intradermal or intravenous injection (e.g. U.S. Pat. No. 4,725,442); aqueous solutions for intrathecal or epidural delivery (e.g. WO2008/036858); swab, droplets, spray or aerosol for transmucosal delivery (e.g. WO2010/025505); aqueous based solutions comprising an extractive solvent in an amount effective to reduce the volatility, vaporisation or evaporation of the volatile anaesthetic for transdermal, topical, mucosal, buccal, rectal, vaginal, intramuscular, subcutaneous, perineural infiltration, intrathecal or epidural delivery (e.g. WO2009/094460, WO2009/094459); compositions suitable for formulation into a medical patch (e.g. WO2014/143964); compositions suitable for formulation as a solution, suspension, cream, paste, oil, lotion, gel, foam, hydrogel, ointment, liposome, emulsion, liquid crystal emulsion and nanoemulsions for topical, intrathecal, epidural, transdermal, topical, oral, intra-articular, mucosal, buccal, rectal, vaginal, intramuscular, intravesical and subcutaneous delivery (e.g. WO2008/070490, WO2009/094460, WO2010/129686); and stable and injectable liquid formulations (WO2013/016511).

The main consideration(s) for the safe storage and handling of volatile liquids commonly include vapor pressure build up, the robustness of the container and the integrity of the container seal(s). The chemical nature of the volatile liquid may also be important if the active agent is capable of permeating, solubilizing or otherwise reacting with the container material(s) upon storage. A number of storage containers for halogenated volatile liquids have been described including: rigid polymeric containers as a replacement for glass vials, such as capped bottles large tanks, shipping containers (e.g. WO1999/034762, WO2012/116187); rigid polymeric bottles fitted with a gasketless valve assembly and pliable containers with a threaded spout for fluid connection to deliver liquid anaesthetics to an anaesthetic machine or vaporizer (e.g. WO2010/135436, WO2013/106608, WO2013/149263, WO2015/034978); a container with a capped membrane for delivering a stored liquid anaesthetic to a vaporizer via a slotted tube (WO2009/117529); and rigid polymeric and aluminium containers optionally coated with materials to impart or enhance vapor barrier characteristics or container inertness (e.g. WO2002/022195, WO2003/032890, WO2010/129796).

Despite the various advances in formulating volatile liquids in non-inhalable forms, such as the halogenated volatile liquids, as well as containers to store them, there still remains a need for inhalable forms of volatile liquids and devices to store and/or administer them to patients.

Attempts to design new inhalers for inhalable medicines in general are ongoing. For example, WO2008/040062 describes a diverse number of inhaler device concepts that depend on complex constructions and moving parts for storing and/or delivering inhalable liquids and powdered solids into a user's mouth or nose. The various devices described are adapted to hold one or two medicament containers in the form of pressurised canisters, ampoules, vials and plungers. The devices are described as being activated by sliding an outer wall of the device in relation to an inner wall of the device to deliver the liquid medication from a medication container. In a number of embodiments, the device includes a moveable mouthpiece which deploys in order to open the air pathway. The device is also described as including one or more one-way valves to provide a unidirectional air flow for one or both inhaled air and exhaled air (a series of one-way valves to direct the flow of inhaled and exhaled air has also been generally described in WO2007/033400 which is an incorporation by reference of the device described in WO1997/003711).

When required for use, the devices of WO2008/040062 are claimed as being capable of releasing the medication by punching means namely two punches to perforate the two frangible ends respectively of a medication container having frangible ends, although various other means are generally described including: pressurised means (e.g. by a pressurised canister); frangible means (e.g. by rupturing an ampoule with a striker or by punching a frangible membrane or seal of a vial with punch means); crushable means (e.g. by crushing a vial with a plunger); dislodging means (e.g. by dislodging an unscrewed cap from a vial); and plunging means (e.g. by plunging the medication from the plunger barrel).

However, inhalable liquids such as halogenated volatile liquids require an effective air chamber into which the vapor may evaporate and allow an effective airflow through the air/vapor chamber for delivery to a patient. Accordingly, embodiments such as those described in, for example, FIGS. 48A, 48B, 48C, 49A, 49B, 50A, 50B, 51A, 51B, 56A, 56B, 57, 58A, 58B, 58C and 58D of WO2008/040062, would not be expected to work in practice as the evaporative means (or wick) is prevented from being effectively exposed to the released liquid by the walls of the liquid storage container itself.

The present invention provides a new inhaler device for the storage and/or administration of inhalable liquids to a patient offering one or more advantages or improvements over known inhalers, particularly inhalers for the delivery of halogenated volatile liquids such as methoxyflurane for use as an analgesic.

SUMMARY

According to a first aspect of the invention there is provided an inhaler device for the delivery of an inhalable liquid to a patient, said device comprising an elongated body wherein the elongated body comprises:
(1) A base end;
(2) A mouthpiece end comprising a mouthpiece chamber;
(3) An air intake chamber comprising a passive evaporation support material for receiving the inhalable liquid from an external liquid storage container and at least one air inlet hole;
(4) A liquid inlet hole for delivering the inhalable liquid from the external liquid storage container into the air intake chamber and onto the passive evaporation support material;
(5) An air exit chamber adapted to internally receive an air filtering means within the elongated body and comprising at least one air outlet hole optionally located in the base end; and
(6) An internal shelf to partially divide the elongated body along its longitudinal axis from the base end and terminating at the mouthpiece chamber to form the floor of the air intake chamber and the roof of the air exit chamber.

The internal shelf enables the accommodation of an air filtering means within the inhaler device. The internal shelf also enables the provision of various ratios of the internal volume of the air intake chamber to the internal volume of the air exit chamber by varying the internal position of the shelf. The internal shelf may be planar or non-planar. The internal shelf may be an integrally formed component of the elongated body.

In one embodiment according to the first aspect, the device further comprises:
(7) A two-way valve abutted to the internal shelf at the mouthpiece end whereupon respiration by a patient through the mouthpiece end:
 (a) upon inhalation by the patient, opens the two-way valve between the air intake chamber and the mouthpiece chamber to deliver the evaporated liquid in the form of a vapor to the patient and closes the two-way valve between the air exit chamber and the mouthpiece chamber; and
 (b) upon exhalation by the patient, opens the two-way valve between the air exit chamber and the mouthpiece chamber to exhaust the expired air and closes the two-way valve between the air intake chamber and the mouthpiece chamber.

In one embodiment according to the first aspect, the air inlet hole and the liquid inlet hole are the same hole. In an alternative embodiment according to the first aspect, the air inlet hole and the liquid inlet hold are separate holes.

In one embodiment according to the first aspect, the liquid inlet hole is located in the roof of the air intake chamber. In an alternative embodiment, the liquid inlet hole is located in the base end of the air intake chamber.

In one embodiment according to the first aspect, the device further comprises a storage chamber for internally holding the liquid storage container wherein the storage chamber is adapted to deliver the inhalable liquid from the liquid storage container into the air intake chamber and onto the passive evaporation support material and the liquid inlet hole is located between the storage chamber and the air intake chamber.

According to a second aspect of the invention there is provided an inhaler device for the delivery of an inhalable liquid to a patient, said device comprising an elongated body wherein the elongated body comprises:
(1) A base end;
(2) A mouthpiece end comprising a mouthpiece chamber;
(3) An air intake chamber comprising a passive evaporation support material for receiving the inhalable liquid and at least one air inlet hole;
(4) A storage chamber for holding an inhalable liquid storage container wherein the storage chamber is adapted to deliver the inhalable liquid from the liquid storage container into the air intake chamber and onto the passive evaporation support material; and
(5) An air exit chamber comprising an air filtering means and at least one air outlet hole;
wherein the storage chamber is located at the base end and the air intake chamber is located intermediate the storage chamber and the mouthpiece chamber and further wherein the air exit chamber is located within the mouthpiece chamber.

In one embodiment according to the second aspect, the liquid inlet hole is located between the storage chamber and the air intake chamber.

There is also provided a device according to the first aspect of the invention wherein the liquid inlet hole is absent and the external liquid storage container is located within the air intake chamber and positioned to release the inhalable liquid onto the passive evaporation support material when opened.

As such, according to a third aspect of the invention there is provided an inhaler device for the delivery of an inhalable liquid to a patient, said device comprising an elongated body wherein the elongated body comprises:

(1) A base end;
(2) A mouthpiece end comprising a mouthpiece chamber;
(3) An air intake chamber comprising a passive evaporation support material for receiving the inhalable liquid from a liquid storage container and at least one air inlet hole;
(4) An air exit chamber adapted to internally receive an air filtering means within the elongated body and comprising at least one air outlet hole optionally located in the base end; and
(5) An internal shelf to partially divide the elongated body along its longitudinal axis from the base end and terminating at the mouthpiece chamber to form the floor of the air intake chamber and the roof of the air exit chamber;

wherein the liquid storage container is located within the air intake chamber and positioned to release the inhalable liquid onto the passive evaporation support material when opened.

In one embodiment according to the first, second, and third aspects of the invention, the air inlet hole further comprises an air intake control means. In one embodiment according to the first, second, and third aspects of the invention, the inhalable liquid storage container is selected from the group consisting of a vial, an ampoule or a vapor impermeable sachet or packet.

In one embodiment according to the first, second, and third aspects of the invention, the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluoromethyl)ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In a preferred embodiment, the inhalable liquid is methoxyflurane for use as an analgesic.

In one embodiment according to the first, second, and third aspects of the invention, the passive evaporation support material is adapted to form a single longitudinal airflow/vapor pathway though the air intake chamber. In another embodiment, the passive evaporation support material is adapted to form at least two independent longitudinal airflow/vapor pathways though the air intake chamber. In a preferred embodiment, the passive evaporation support material is adapted to form three or more independent longitudinal airflow/vapor pathways though the air intake chamber.

DETAILED DESCRIPTION

Figure 1:
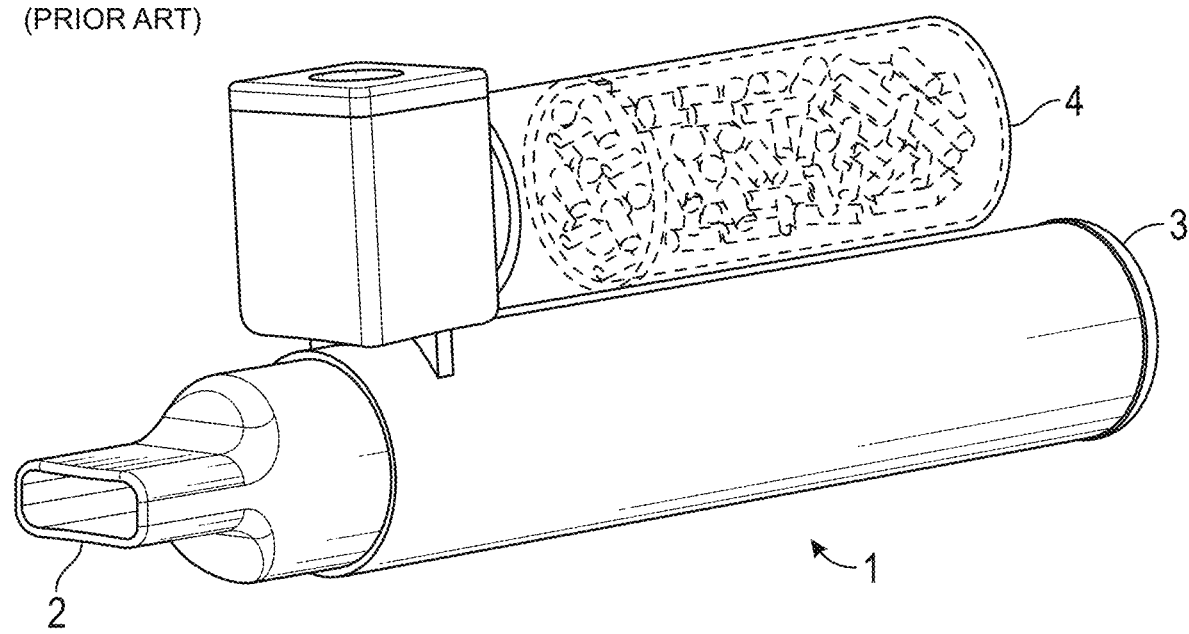
FIG. 1 shows a prior art inhaler device, referred to as the Green Whistle™ inhaler device (Medical Developments International Limited) that is currently used to administer methoxyflurane.

Inhaler devices that are useful for administering inhalable liquids may be generally considered to operate by either passive or active means in order to deliver the active agent(s) to a patient. Inhaler devices with active means may include pressurized, moving, mechanical, heating and/or electrical means to, for example, nebulise, vaporize and/or generally deliver the active agent(s). In contrast, inhaler devices with passive means rely solely on the vaporisation or evaporation of the active agent(s) at ambient conditions and respiration of the patient to deliver the active agent(s).

The Analgizer™ inhaler device (Abbott Laboratories Corporation) is an example of a device that operates by passive means to deliver an inhalable liquid. According to the USPTO TESS database, the Analgizer™ was a registered, now lapsed, trademark in respect of an inhaler for the supervised self-administration of inhalation anaesthesia and was first used in 1968. The Analgizer™ was a very simple device that consisted of a white cylindrical polyethylene open-ended tube having a mouthpiece and an absorbent wick of polypropylene which was tightly rolled into a 'Swiss-roll' shape, i.e. cross-sectional view. The inhalation anaesthetic, methoxyflurane (15 mL), was poured into the open ended base of the inhaler and onto the tightly wound wick, just prior to use. A patient was then able to self-administer the liquid anaesthetic by inhaling through the mouthpiece.

The Green Whistle™ inhaler device (Medical Developments International Limited) was subsequently developed during the 1990s and has since been used in Australia for the delivery of Penthrox®/™ (methoxyflurane) as an analgesic (1.5 mL or 3 mL, storage brown glass vial container with screw cap). Although similar in its simplicity of design to the Analgizer™, the Green Whistle™ device includes certain functional improvements such as the inclusion of a one-way valve at the base end to prevent drug vapor loss from the device upon patient exhalation and an activated carbon ('AC') chamber designed to be externally fit into a dilution hole in the mouth piece to filter exhaled drug vapors. Additional design modifications to the base end included the introduction of cap lugs to assist removal of the cap from the glass vial used to store the drug dose to be delivered, a dome to facilitate the spread of the poured liquid onto the 'S-shaped' wick (i.e. cross-sectional view) or, in the alternative to a dome, an inlet nipple to allow for the attachment of a breathable gas line to direct the gas through the device. The Green Whistle™ device is designed for single patient use.

Methoxyflurane (Penthrox®/™, Medical Developments International Limited) offers a non-narcotic, i.e. non-opioid analgesic alternative to common analgesics such as morphine and fentanyl. Methoxyflurane also presents an alternative to analgesics which are administered in oral tablet form or intraveneously to a patient and may therefore be particularly useful when rapid pain relief is required in clinical, surgical (e.g. pre- and post-operative) and/or emergency settings (e.g. emergency department and triage management as well as by first-responders such as paramedics and search and rescue teams). However, the Green Whistle™ device is currently the only device that is commercially available to administer methoxyflurane. According to the device's instructions for use, the administrator is required to hold the methoxyflurane bottle upright to use the base of the inhaler to loosen the bottle cap and then to remove the cap by hand before tilting the inhaler to a 45° angle and pouring the contents of the bottle into the base while rotating the device. An AC-chamber may be optionally fitted externally to the device either beforehand or afterwards. While the device is effective, the number of steps and separate components may present handling difficulties for the administrator or self-administrator, for example, in high-stress and/or emergency settings.

The present invention provides a new inhaler device for the storage and/or administration of inhalable liquids to a patient, such as halogenated volatile liquids, particularly methoxyflurane for use as an analgesic, the device having one or more advantages or improvements over known inhalers.

Definitions

Unless otherwise herein defined, the following terms will be understood to have the general meanings which follow.

'Active agent' refers to therapeutic agents and non-therapeutic agents and compounds, formulations and compositions comprising them.

'Alleviate', 'Alleviation' and variations thereof refers to relieving, lessening, reducing, ameliorating or an improvement in the symptom(s) and/or underlying cause(s) of a condition and/or disease in a patient.

'Delivery dose' refers to the dose of inhalable liquid or active agent for administration to a patient.

'Filter', 'Filtering' and variations thereof refers to the ability of a substance to absorb, adsorb, capture, trap, scavenge, scrub or partially or entirely remove the inhalable volatile liquid vapor from the exhaled breath of a patient upon exhalation.

'Halogenated volatile liquids' refers to volatile liquids which (i) comprise at least one halogen atom selected from the group consisting of a chlorine (CI), bromine (Br), fluorine (F) and iodine (I) atoms, or (ii) comprise an active agent which comprises at least one halogen atom selected from the group consisting of a chlorine (CI), bromine (Br), fluorine (F) and iodine (I) atoms. In some embodiments, halogenated, particularly fluorinated, hydrocarbons and halogenated, particularly fluorinated, ethers may be preferred. In some embodiments, halogenated ethers may be particularly preferred and include but are not limited to, halothane (2-bromo-2-chloro-1,1,1-trifluoroethane), sevoflurane (fluoromethyl-2,2,2-trifluoro-1-(trifluromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether).

'Inhalable liquid' refers to liquids that comprise active agents or that are themselves the active agent and that are readily inhalable or capable of being or adapted to be inhaled by a patient. In some embodiments, inhalable volatile liquids, particularly halogenated volatile liquids are preferred.

'Inhalation', 'Inhalable' and variations thereof refers to the intake of, for example but not limited to air, breathable gases, inhalable liquids, by a patient and includes both oral and nasal inhalation. In some embodiments, oral inhalation is particularly preferred.

'Patient' refers to both human and veterinary patients. In some embodiments, human patients may be particularly preferred. Reference to a patient will therefore be understood to mean the person or animal to whom the inhalable liquid is administered to and in the case of human patients, will be understood to include administration by self-administration.

'Pharmaceutical agent' refers to a drug, or a compound, formulation or composition that comprises a drug, for the treatment of symptom(s) and/or underlying cause(s) of a condition and/or disease in a patient. The term pharmaceutical agent may be used interchangeably with therapeutic agent or active agent.

'Respiratory', 'Respirational' and variations thereof refers to the act of respiring, breathing, inhaling and exhaling, such as for example but not limited to air, breathable gases, inhalable liquids and active ingredients, by a patient.

'Room temperature' refers to ambient temperatures which may be, for example, between 10° C. to 40° C. but more typically between 15° C. to 30° C.

'Therapeutic agent' refers to an active agent, or a compound, formulation or composition (including biological compounds, formulations and compositions) that comprises an active agent, that is capable of treating a patient or offers a therapeutic or medical benefit to a patient or that has or that requires regulatory and/or marketing approval for therapeutic use in a patient. Therapeutic agents include pharmaceutical agents. In contrast, a 'Non-therapeutic agent' will be understood to mean an active agent which may not have or require regulatory and/or marketing approval for a therapeutic use such as, for example, smokeless tobacco products and electronic cigarettes, or does not have a recognised or identified therapeutic use but may be used by a patient for a non-therapeutic reason such as general health, wellbeing or physiological benefit such as, for example, nutraceutical products.

'Treat', 'Treatment' and variations thereof refers to the alleviation, modulation, regulation or halting of the symptom(s) and/or underlying cause(s) of a condition and/or disease in a patient. In some embodiments treatment may include preventative or prophylactic treatment.

'Volatile liquids' refers to substances that predominantly exist in a liquid form but readily form vapors, evaporate or vaporize such that they partially exist in a vapor form under ambient conditions for example, at room temperature and at normal atmospheric pressures.

EMBODIMENTS

Embodiments will now be described with reference to the non-limiting examples. There is provided an inhaler device for the delivery of an inhalable liquid to a patient, said device comprising an elongated body wherein the elongated body comprises:

(1) A base end;
(2) A mouthpiece end comprising a mouthpiece chamber;
(3) An air intake chamber comprising a passive evaporation support material for receiving the inhalable liquid from an external liquid storage container and at least one air inlet hole;
(4) A liquid inlet hole for delivering the inhalable liquid from the external liquid storage container into the air intake chamber and onto the passive evaporation support material;
(5) An air exit chamber adapted to internally receive an air filtering means within the elongated body and comprising at least one air outlet hole optionally located in the base end; and
(6) An internal shelf to partially divide the elongated body along its longitudinal axis from the base end and terminating at the mouthpiece chamber to form the floor of the air intake chamber and the roof of the air exit chamber.

It will be understood that the use of the terms 'floor' and 'roof' of the air intake and air exit chambers as used herein are relative terms only and used solely as a point of reference with respect to the orientation of the device as intended for normal operation. It is envisaged that in normal operation, the device will be oriented so that the air intake chamber is capable of receiving the inhalable liquid, for example, by pouring from an external liquid storage container.

In one embodiment, the air inlet hole further comprises an air intake control means. In a further embodiment the air intake control means is an adjustable cover.

In one embodiment the air inlet hole and the liquid inlet hole are the same hole. In an alternative embodiment the air inlet hole and the liquid inlet hold are separate holes.

In one embodiment the liquid inlet hole is located in the roof of the air intake chamber. In an alternative embodiment the liquid inlet hole is located in the base end of the air intake chamber.

In one embodiment, the device comprises a two-way valve abutted to the internal shelf at the mouthpiece end to direct the airflow/vapor pathway through the device whereupon respiration by a patient through the mouthpiece end:
(a) upon inhalation by the patient, opens the two-way valve between the air intake chamber and the mouthpiece chamber to deliver the evaporated liquid in the form of a vapor to the patient and closes the two-way valve between the air exit chamber and the mouthpiece chamber; and
(b) upon exhalation by the patient, opens the two-way valve between the air exit chamber and the mouthpiece chamber to exhaust the expired air and closes the two-way valve between the air intake chamber and the mouthpiece chamber.

In one embodiment the two-way valve abuts up against the internal shelf and is connected thereto. In another embodiment the two-way valve is inserted to abut up against the internal shelf without being connected thereto.

In an alternative embodiment is the device optionally comprises one or more one-way valves to direct the airflow/vapor pathway through the device. In a further embodiment there is provided a one-way valve between the air intake chamber and the mouthpiece chamber and/or a one-way valve between the mouthpiece chamber and the air exit chamber.

Examples of liquid storage containers which may be suitable for use in the present in invention include, but are not limited to vials, ampoules or vapor impermeable sachets or packets. The liquid storage containers may be made from glass or one or more materials as described herein that are compatible with the storage of halogenated volatile liquids such as, for example, vapor impermeable films, polymers, composites, metals and combinations thereof.

To facilitate the ease of administration, in particular self-administration, the device may be pre-loaded with a storage container of the inhalable liquid.

Accordingly, in another embodiment the device further comprises a storage chamber for internally holding an inhalable liquid storage container wherein the storage chamber is adapted to deliver the inhalable liquid from the liquid storage container into the air intake chamber and onto the passive evaporation support material.

In one embodiment, the storage chamber is movable relative to the air intake chamber. In one embodiment the storage container is movably connected to the base end of the elongated body.

In one embodiment, the storage chamber comprises an unopened inhalable liquid storage container in a first position wherein the storage chamber is movable to a second position to open the liquid storage container to deliver the inhalable liquid from the liquid storage container into the air intake chamber and onto the passive evaporation support material.

The type of liquid storage container will determine how it may be opened to deliver or release the inhalable liquid onto the passive evaporation support material. For example, a vial with a screw cap lid may be opened by unscrewing the lid, a vial with a plug may be opened by unplugging i.e. by pulling out the plug or pushing it into the vial, a vial sealed with a vapor impermeable film may be opened by puncturing or piercing the film, an ampoule may be opened by snapping or crushing and vapor impermeable sachets or packets may be opened by ripping, unpeeling, pulling, perforating or tearing.

In one embodiment, the liquid storage container is selected from the group consisting of a vial (preferably a glass vial), an ampoule (preferably a glass ampoule) and a vapor impermeable sachet or packet.

In one embodiment the storage chamber delivers the inhalable liquid into the air intake chamber by pushing, sliding or rotating the liquid storage container into an opened position.

In one embodiment the liquid storage container is selected from a vial comprising a screw cap lid and the storage chamber is adapted to deliver the inhalable liquid from the vial into the air intake chamber and onto the passive evaporation support material by rotating the storage chamber relative to the air intake chamber to unscrew cap lid to open the vial by moving the vial from a first position into a second position.

In one embodiment the liquid storage container is a vial with a plug and the storage chamber is adapted to deliver the inhalable liquid from the vial into the air intake chamber and onto the passive evaporation support material by pushing the storage chamber relative to the air intake chamber to push the plug into the vial to open the vial by moving the vial from a first position into a second position.

In one embodiment the liquid storage container is a vial sealed with a vapor impermeable film and the storage chamber is adapted to deliver the inhalable liquid from the vial into the air intake chamber and onto the passive evaporation support material by puncturing or piercing the film to open the vial by moving the vial from a first position into a second position.

In one embodiment the liquid storage container is an ampoule and the storage chamber is adapted to deliver the inhalable liquid from the ampoule into the air intake chamber and onto the passive evaporation support material by rotating the storage chamber relative to the air intake chamber to snap the ampoule to open the ampoule by moving the ampoule from a first position into a second position. In one embodiment the liquid storage container is a vapor impermeable sachet or packet and the storage chamber is adapted to deliver the inhalable liquid from the sachet or packet into the air intake chamber and onto the passive evaporation support material by moving the storage chamber relative to the air intake chamber to rip, perforate or tear the sachet or packet to open the sachet or packet by moving the ampoule from a first position into a second position.

In one embodiment, the storage sachet is entirely formed from a vapor impermeable film adapted to sealingly store the halogenated volatile liquid. When the storage sachet is entirely formed from a vapor impermeable film it may be sealed by sealing an outer perimeter portion of the vapor impermeable film to itself. In another embodiment, the storage sachet is formed from a vapor impermeable film having a base portion wherein the vapor impermeable film is adapted to sealingly store the halogenated volatile liquid together with the base portion and further wherein the base portion is rigid or semi-rigid.

In one embodiment the base portion is formed from a polymer as described herein. To reduce manufacturing costs the base portion and the inhaler body may be formed from the same polymer. The base portion will typically be planar but may optionally comprise a receptacle portion for receiving the halogenated volatile liquid. When the storage sachet is formed from a vapor impermeable film having a base portion it may be sealed by sealing a perimeter edge of the base portion with an outer perimeter portion of the vapor impermeable film. Where the base portion comprises a receptacle portion, the perimeter edge of the base portion may be a lip of the receptacle. Further, the receptacle portion may form part of the inhaler device itself as further described in embodiments herein.

In one embodiment the storage sachet comprises an outer perimeter portion for fastening to the inhaler body.

When the storage sachet is positioned within the inhaler device for administration of the halogenated volatile liquid to the patient, the storage sachet may be opened by removing the vapor impermeable film or a portion thereof by peeling, pulling, tearing, ripping, perforating, puncturing or piercing.

To assist opening the storage sachet by peeling, pulling, tearing or ripping, the storage sachet may optionally comprise a pull tab which may protrude through an opening in the inhaler body, such as an air inlet opening or air exit opening, whereby it can be gripped and pulled by the user to release the inhalable liquid thereby avoiding movable components of the device itself to open the storage sachet. Accordingly, in one embodiment the storage sachet comprises a pull tab adapted to open the storage sachet by peeling, pulling, tearing or ripping the vapor impermeable film. The pull tab may be made from any suitable material capable of connecting to the vapor impermeable film and withstanding the pulling or peeling forces required to open the storage sachet. The pull tab may be integrally formed and connected to the vapor impermeable film and in one embodiment the pull tab is integrally formed from the vapor impermeable film. The pull tab may also be independently formed and connected to the vapor impermeable film and in one embodiment the pull tab is made from a different material to the vapor impermeable film.

To assist opening the storage sachet by perforating, puncturing or piercing, the sachet may engage with the inhaler body which may optionally comprise a perforating, puncturing or piercing means operable by movement of the device.

There is also provided an inhaler device for the delivery of an inhalable liquid to a patient, said device comprising an elongated body wherein the elongated body comprises:
(1) A base end;
(2) A mouthpiece end comprising a mouthpiece chamber;
(3) An air intake chamber comprising a passive evaporation support material for receiving the inhalable liquid and at least one air inlet hole;
(4) A storage chamber for holding an inhalable liquid storage container wherein the storage chamber is adapted to deliver the inhalable liquid from the liquid storage container into the air intake chamber and onto the passive evaporation support material; and
(5) An air exit chamber comprising an air filtering means and at least one air outlet hole;
wherein the storage chamber is located at the base end and the air intake chamber is located intermediate the storage chamber and the mouthpiece chamber and further wherein the air exit chamber is located within the mouthpiece chamber.

In one embodiment, the air inlet hole further comprises an air intake control means. In a further embodiment the air intake control means is an adjustable cover.

There is also provided a device according to the first aspect of the invention wherein the liquid inlet hole is absent and the external liquid storage container is located within the air intake chamber and positioned to release the inhalable liquid onto the passive evaporation support material when opened.

Accordingly, there is provided an inhaler device for the delivery of an inhalable liquid to a patient, said device comprising an elongated body wherein the elongated body comprises:
(1) A base end;
(2) A mouthpiece end comprising a mouthpiece chamber;
(3) An air intake chamber comprising a passive evaporation support material for receiving the inhalable liquid from a liquid storage container and at least one air inlet hole;
(4) An air exit chamber adapted to internally receive an air filtering means within the elongated body and comprising at least one air outlet hole optionally located in the base end; and
(5) An internal shelf to partially divide the elongated body along its longitudinal axis from the base end and terminating at the mouthpiece chamber to form the floor of the air intake chamber and the roof of the air exit chamber;
wherein the liquid storage container is located within the air intake chamber and positioned to release the inhalable liquid onto the passive evaporation support material when opened.

The present device is considered to provide one or more advantages or improvements as described herein.

Without wishing to be bound by theory, the inventors believe that the amount of vapor that is able to form in the air intake chamber and the volume and rate of air flow over the passive evaporation support material are important considerations for drug delivery and patient administration. It may be therefore be desirable to control the air intake of the inhaler device when in use. This may, in part, assist in preventing a patient receiving a first inhaled dose of the vapor from the air intake chamber that is too strong, unpalatable or otherwise generally off-putting thereby discouraging the patient to continue use. Accordingly, it is considered that one advantage of the present device may be the ability to control the amount of vapor that is delivered to the patient by providing an air intake control means to control the volume of air that is drawn into the air intake chamber through the air inlet hole and across the surface(s) of the passive evaporation support material when a patient inhales through the mouthpiece.

In one embodiment, the air intake control means is in the form of an adjustable cover located to adjustably cover (i.e. to open and close) the air inlet hole(s). The air inlet hole(s) may be formed in a number of ways when the adjustable cover is opened, for example, by groove(s) or hole(s) in the air intake chamber which may be exposed to provide an air flow pathway or by groove(s) or hole(s) which may optionally align with groove(s) or hole(s) in the adjustable cover.

When the device is required for patient use, the adjustable cover may be gradually adjusted from a closed position where it completely covers the air inlet hole(s), to a partially opened or fully opened position to enable the air to flow into the air intake chamber and across the surface(s) of the passive evaporation support material to deliver the vapor to the patient as the patient inhales. In one embodiment the adjustable cover is selected from the group consisting of a rotatable end cap cover located at the base end of the elongated body; a sleeve cover rotatably mounted around the circumference of the elongated body; a slideable cover and a flap cover. The rotatable end cap cover and rotatable sleeve cap cover may be detachably fastened to rotatingly engage with the rest of the elongated body of the device by, for example, a screw thread arrangement or a snap-fit joint arrangement.

The adjustable cover may also advantageously enable the device to be temporarily and/or partially sealed when the adjustable cover is in a closed position to prevent excess vapor escaping through the air inlet hole(s) during intermittent use. Accordingly, in one embodiment the adjustable cover is a rotatable end cap optionally comprising a wad insert. The wad insert may comprise a compressible material and a vapor impermeable film or foil to assist with providing a tight seal when the rotatable end cap is closed. Examples of compressible materials include but are not limited to polymeric foams or sponges such as LDPE.

Examples of vapor impermeable films include but are not limited to polymeric films, metal foils (such as, for example, aluminium, nickel and alloys thereof) and combinations, including co-extruded polymeric films and/or foils such as laminate films, thereof. In one embodiment the vapor impermeable film is a single layer selected from a polymeric film or a metal foil. In another embodiment the vapor impermeable film is a laminate film comprising two or more layers selected from a polymeric film, a metal foil and combinations, including co-extruded polymeric films and/or foils, thereof. The laminate film may comprise a weldable layer made from a suitable weldable foil or polymeric film such as, for example, LLDPE. A weldable layer may assist with sealing the layers of a laminate together and/or sealing a vapor impermeable film comprising a weldable layer to the device. Processes suitable for welding include thermal and ultrasonic welding.

In one embodiment the polymeric film has a MVTR of less than 100 g/m$^2$/24h, preferably less than 50 g/m$^2$/24 h. In one embodiment the polymeric film comprises a polymer selected from the group consisting of a polyolefin, a polymeric phthalate, a fluorinated polymer, a polyester, a nylon, a polyvinyl, a polysulfone, a natural polymer and combinations, including co-extruded polymers thereof including biaxially orientated polymers such as, for example, biaxially orientated polypropylene (BOPP). In one embodiment the polymeric film comprises a polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof.

In one embodiment the vapor impermeable film comprises PET. In another embodiment the vapor impermeable film comprises PET and a metal foil layer, preferably an aluminium foil layer. In one embodiment the vapor impermeable film comprises metalised PET (Met PET).

In one embodiment the vapor impermeable film comprises a co-extruded polymer layer adhered to a metalised PET layer adhered to an externally peelable LLDPE layer. In a further embodiment the co-extruded polymer layer is a biaxially orientated polymer, preferably BOPP. In another embodiment the vapor impermeable film comprises a layer of BOPP adhered to a metalised PET layer adhered to an externally peelable LLDPE layer.

In another embodiment, the adjustable cover optionally comprises vents to restrict rather than completely prevent the intake of air through the air inlet hole(s) when the adjustable cover is in a closed position.

In use, the air inlet hole(s) may be opened in a number of ways. The adjustable cover may be opened, for example, by twisting, turning, rotating, unscrewing, sliding, popping, pulling, pivoting or flipping the adjustable cover open relative to the elongated body. The air flow pathway may be adjustably controlled by the degree of twisting, turning, rotating, unscrewing, popping, pulling, pivoting or sliding of the adjustable cover relative to the elongated body to provide partially opened or fully opened air inlet opening(s). The adjustable cover may comprise one or more air inlet opening(s) to adjustably align with the air inlet opening(s) in the air intake chamber.

It may also be desirable to increase or decrease the size of the air intake chamber relative to the air exit chamber without having to substantially increase the overall size of the device. Accordingly, it is considered that one advantage of the present device may be the ability to provide different ratios of air intake chamber size to air exit chamber size depending on design requirements. In one embodiment, the internal shelf is positioned within the elongated body to divide the internal volumes of the air intake chamber to the air exit chamber in a ratio selected from within the range 5:95 to 95:5 or 10:90 to 90:10. In one embodiment, the ratio is selected from the group consisting of 5:95, 10:90, 15:85; 20:80, 25:75, 30:70, 35:65, 40:60, 45:55; 50:50, 55:45, 60:40, 65:35; 70:30, 75:25; 80:20, 85:15, 90:10 and 95:5. Ratios in-between are also contemplated.

In one embodiment the internal shelf is positioned to provide an internal volume of the air intake chamber to an internal volume of the air exit chamber in a ratio selected from the group consisting of 50:50, 55:45, 60:40, 65:35; 70:30, 75:25; 80:20, 85:15, 90:10 and 95:5 and vice versa. In one embodiment the relative size of the air intake chamber to the air exit chamber is >50%. In a further embodiment the internal volume of the air intake chamber to the internal volume of the air exit chamber is in a ratio selected from the group consisting of 55:45, 60:40, 65:35; 70:30 and 75:25. In another embodiment the relative size of the air intake chamber to the air exit chamber is <50%. In a further embodiment the internal volume of the air intake chamber to the internal volume of the air exit chamber is in a ratio selected from the group consisting of 45:55, 40:60, 35:65; 30:70 and 25:75. In one embodiment the ratio is 50:50.

The internal shelf may be planar or non-planar. In one embodiment the internal shelf is planar. However, in order to achieve the desired ratios while still accommodating the passive evaporative support material within the air intake chamber and the air filtering means within the air exit chamber, a non-planer configuration may be preferred. In one embodiment the internal shelf is non-planar. Examples of non-planar configurations may comprise one or more recessed portions or adopt the same or a similar cross-sectional profile as the elongated body, for example a semi-circular cross-section when the elongated body is cylindrical. In one embodiment the internal shelf is planar or non-planar and optionally comprises one or more recessed portions. In one embodiment the internal shelf is non-planar and adopts the same or a similar cross-sectional profile to the elongated body.

It may also be desirable to direct the site(s) of deposition of the poured liquid onto the passive evaporation support material and to improve its distribution once deposited. Accordingly, it is considered that one advantage of the present device is the ability to direct the site of deposition of the poured liquid onto the passive evaporation support material and/or improve its distribution once deposited. In one embodiment, the liquid inlet hole comprises an optional liquid inlet guide. Without wishing to be bound by theory, the inlet guide is considered to offer the advantage(s) of being able to improve the distribution of the poured liquid throughout the passive evaporation support material by being designed to disrupt or break the surface tension of the poured liquid as it leaves the inlet guide and/or direct the location of its initial site(s) of contact with the evaporative means. The inlet guide may be in the form of a funnel, gutter, channel, chute or the like.

The evaporative means within the Analgizer™ and Green Whistle™ devices essentially extends longitudinally throughout their entire device length. Further, those devices do not accommodate an internally located air exit chamber adapted to internally receive an air filtering means within the elongated body. Accordingly, it is considered that one advantage of the present device is the ability to maintain a similar overall size or smaller size compared to the prior inhaler devices for administering methoxyflurane with the added benefit of internally accommodating an air filtering means and without adversely affecting the delivery of the vapor from the air intake chamber.

The Green Whistle™ that is currently on the market has a length of 152 mm and a diameter of 27 mm and the externally fitted AC chamber has length of 78 mm, a width of 25 mm and a height of 35 mm. The dimensions of the prototype devices of the present invention which comprise an internally located air exit chamber adapted to internally accommodate an air filtering means such as an AC chamber are of similar length and diameter to the Green Whistle device.

Due to the presence of the dual chambers contained internally within the device, i.e. air intake and exit chambers, the smaller size of the air intake chamber when compared to similar known devices has, in some embodiments, necessitated the design of suitable passive evaporation support material by the inventors. The size and shape of the passive evaporation support material may be selected having particular regard to the overall size and shape of the device and air intake chamber.

In one embodiment the passive evaporation support material is adapted to form a single longitudinal airflow/vapor pathway though the air intake chamber. In another embodiment, the evaporative means is adapted to form at least two independent longitudinal airflow/vapor pathways though the air intake chamber. In a preferred embodiment, the evaporative means is adapted to form three or more independent longitudinal airflow/vapor pathways though the air intake chamber.

In one embodiment the passive evaporation support material is adapted to form a single longitudinal airflow/vapor pathway though the air intake chamber, the form being selected from the group consisting of a planar lining relative to the floor of the air intake chamber; a partial lining of the internal surface of the air intake chamber; and a full lining of the internal surface of the air intake chamber.

Figure 2A:
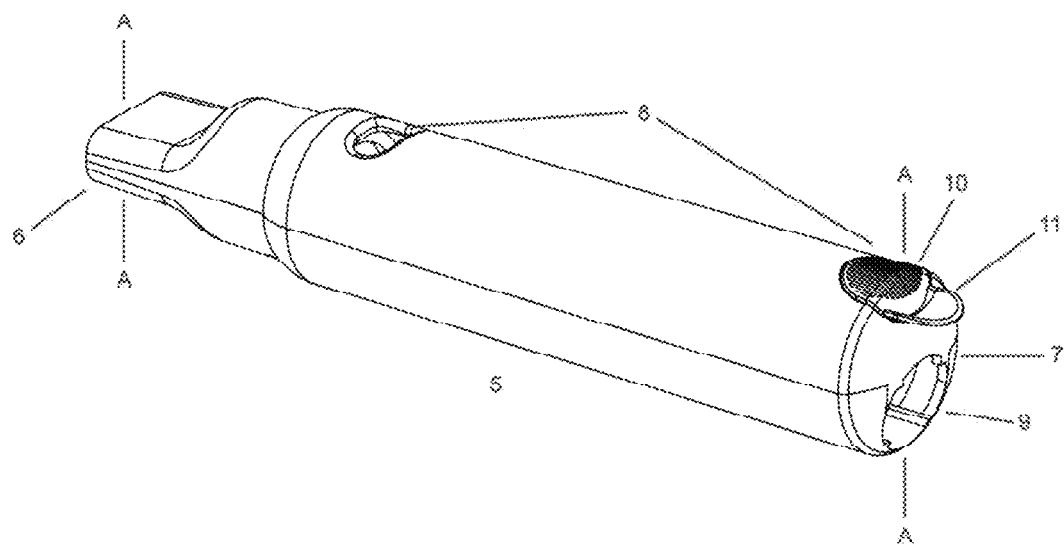
FIG. 2 shows an inhaler device according to an embodiment of the invention (FIG. 2A) and a cross-sectional view of the device along line A-A (FIG. 2B).
Figure 2B:
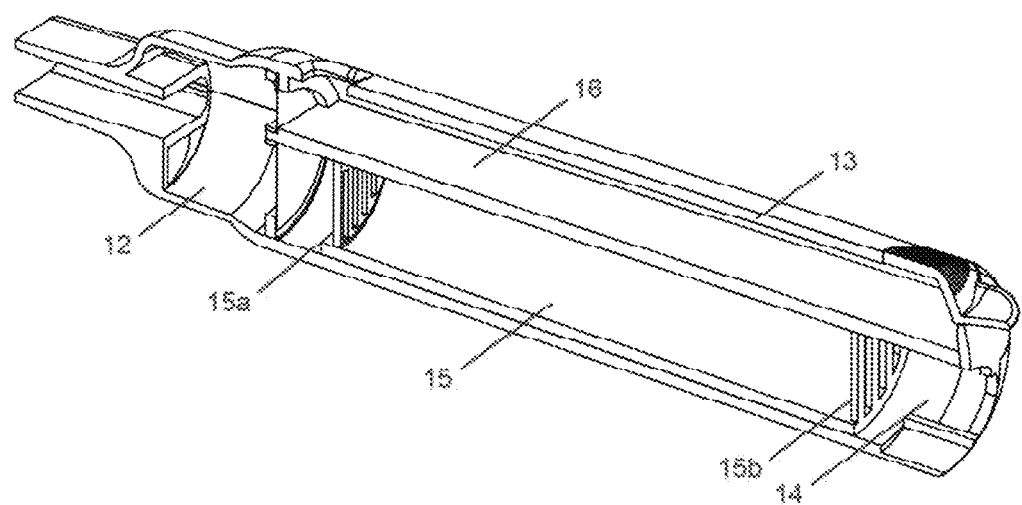
Figure 3A:
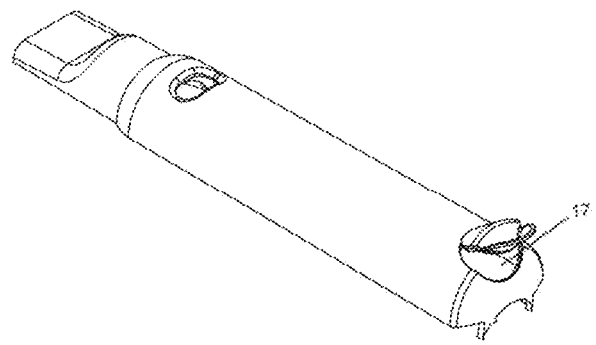
FIG. 3 shows an exploded view of the inhaler device of FIG. 2A to better illustrate the sections of the elongated body that comprise an air intake chamber (FIG. 3A), an internal shelf attached to a cartridge comprising an air filtering substance and the components of a two-way valve (FIG. 3B) and an air exit chamber (FIG. 3C).
Figure 3B:
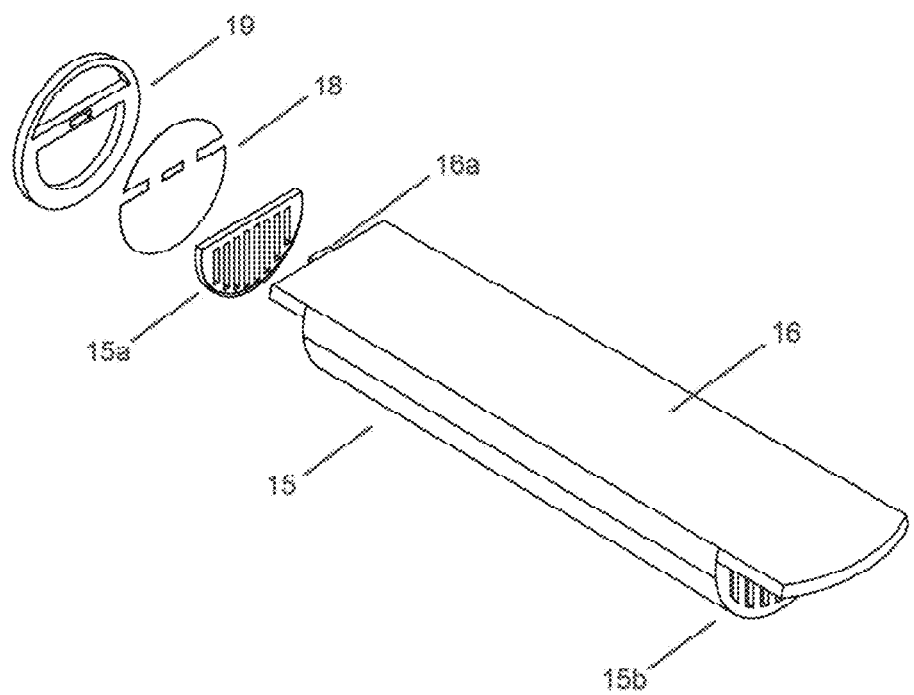
Figure 3C:
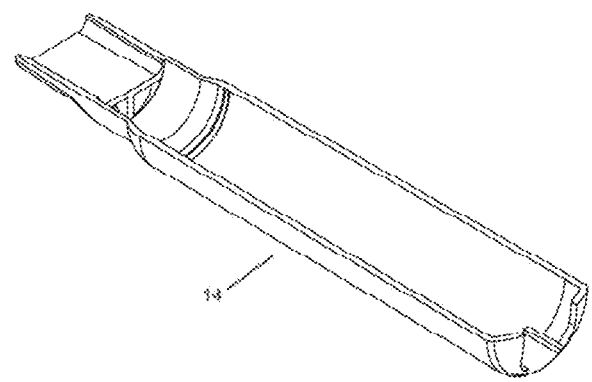

In another embodiment the passive evaporation support material is adapted to form at least two independent longitudinal airflow/vapor pathways, preferably three or more independent longitudinal airflow/vapor pathways, through the air intake chamber. Numerous examples of cross-sectional shapes which are capable of forming at least two, preferably three or more independent longitudinal airflow/vapor pathways may be envisaged, some of which follow. The two, preferably three or more independent longitudinal airflow/vapor pathways may be formed by the passive evaporation support material adopting a cross-sectional shape selected from a letter of the alphabet or a single digit number such as, for example although not limited to, an A-shape, B-shape, S-shape, Z-shape, figure-2, figure-5 and figure-8 which are capable of forming at least two independent airflow/vapor pathways, and a K-shape, M-shape, V-shape, W-shape, X-shape, Y-shape and figure-3 which are capable of forming three or more independent longitudinal airflow/vapor pathways through the air intake chamber.

In one embodiment the passive evaporation support material is adapted to provide three or more independent longitudinal airflow/vapor pathways. The pathways may be formed as independent conduits through the passive evaporation support material itself or the pathways may be formed by the passive evaporation support material making contact with an internal surface of the air intake chamber. Accordingly, in one embodiment, the passive evaporation support material comprises three or more longitudinal conduits wherein the conduits are formed within the passive evaporation support material or are formed by the passive evaporation support material together with an internal surface of the air intake chamber or a combination thereof.

Passive evaporation support material which are adapted to provide three or more independent longitudinal airflow/vapor pathways may be particularly suited to small chamber sizes and/or embodiments where the air intake chamber is intermediate the storage chamber and the mouthpiece chamber. Accordingly, it is considered that one advantage of the present device is the ability to distribute the poured liquid onto and throughout the passive evaporation support material by providing an increased number of air/vapor pathways and a larger area of the passive evaporation support material for the poured liquid to first contact which, for example avoids the need to rotate the device while pouring the liquid as is required by the Green Whistle™ inhaler device (Medical Developments International Limited) that is currently used to administer methoxyflurane.

In one embodiment, the passive evaporation support material has a central portion with three or more radial arms extending from the central portion to an internal surface of the air intake chamber to form three or more longitudinal conduits. One example is shown in FIG. 8 whereby the passive evaporation support material (57) comprises three or more radial arms extending from a central portion to an internal surface of the vapor chamber to form three or more longitudinal conduits. Without wishing to be bound by theory it is considered that the radial arms assist evaporation from a surface of the passive evaporation support material by facilitating the spread of liquid outwardly from the central portion towards the air intake chamber walls and throughout its length towards the mouthpiece chamber.

In one embodiment the passive evaporation support material comprises a staving means to open the storage container and release its liquid contents onto the evaporative means. Examples of staving means may include but are not limited to a rod with a blunted end adapted to push a container seal into the container to release the liquid contents or a rod with a tapered or pointed end to pierce, puncture or break a container seal to release the liquid contents.

The passive evaporation support material may be made from any material that is suitable for absorbing the inhalable liquid and passively releasing it as a vapor. Materials which have wicking properties are particularly preferred passive evaporation support material for use in the present device. Wicking properties will generally be understood to include the ability of a material to facilitate or enhance the rate of evaporation or vaporisation of a liquid from its surface by distributing the liquid, whether by drawing, spreading, pulling or otherwise, throughout the material from its initial point of contact and/or as it evaporates from an exposed surface area of the material. Accordingly, in one embodiment the passive evaporation support material is a wicking material. In one embodiment the wicking material is a wicking felt or a porous polymeric material. In a preferred embodiment the wicking material is a polypropylene wicking felt.

The present device is considered to be particularly useful for storing and administering a halogenated volatile liquid, particularly methoxyflurane for use as an analgesic. Accordingly, in one embodiment the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluroromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In a preferred embodiment, the inhalable liquid is methoxyflurane for use as an analgesic.

Suitable delivery doses of inhalable liquid for administration to a patient by the present device may be determined by reference to, for example, regulatory approved dosage amounts. Suitable delivery doses of methoxyflurane for use as an analgesic will typically be less than 15 mL and preferably less than 12 mL. In one embodiment the delivery dose is selected from the group consisting of 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL, 10.5 mL, 11 mL, 11.5 mL and 12 mL. In one embodiment the delivery dose of methoxyflurane for administration by the present device is selected from the group consisting of 1.5 mL, 3 mL and 6 mL.

It may also be desirable to filter the exhaled air which contains a proportion of the inhaled vapor in order to reduce the exposure of others in close proximity to the patient during administration. Accordingly, it is considered that one advantage of the present device is the provision of an air exit chamber adapted to internally receive an air filtering means. In one embodiment, the air exit chamber comprises the air filtering means.

Examples of an air filtering means include but are not limited to activated carbon ('AC'), preferably in granular form. In one embodiment the air filtering means comprising activated carbon, preferably in a granular form. In another embodiment the air filtering means is a cartridge comprising an air filtering substance such as activated carbon ('AC'), preferably in granular form and/or one or more filters such as optimised filter paper(s). The cartridge may be insertably removable from the air exit chamber or may be integrally formed therein. In one embodiment the cartridge comprising the air filtering substance(s) is insertably removable from the air exit chamber by for example, a sliding guide means in the air exit chamber wall(s) and/or in the internal shelf. In another embodiment, the cartridge comprising the air filtering substance(s) is integrally formed with the air exit chamber wall(s) and/or the internal shelf. In one embodiment the air exit chamber is adapted to internally receive activated carbon granules. In a further embodiment the activated carbon granules are present within the air exit chamber.

The device may be made from various materials. However, suitable material(s) may be selected by considering whether they are chemically inert, stable and impervious with reference to the inhalable liquid to be stored and/or delivered. Material(s) may also be selected based on their suitability for medical device applications such as by reference to whether they meet approved standards for medical-grade human use by a regulatory authority like the FDA.

It is envisaged that the present device will be particularly useful for storing and/or administering halogenated volatile liquids. Accordingly, in one embodiment, the device is made from one or more materials that are compatible with the storage and/or delivery of halogenated volatile liquids to a patient, in particular methoxyflurane for use as an analgesic.

Examples of materials which may be suitable for making the present device include but are not limited to polymers (including homopolymers and heteropolymers i.e. co-polymers), composites (including nanocomposites), metals (including alloys thereof) and combinations thereof. In one embodiment, the device is made from polymers (including homopolymers and heteropolymers i.e. co-polymers), composites (including nanocomposites such as polymers in combination with clay), metals (including aluminium and alloys thereof) and combinations thereof. In a further embodiment, the device is optionally internally lined or coated with one or more material(s) selected from the group consisting polymers (including homopolymers and heteropolymers i.e. co-polymers), composites (including nanocomposites such as polymers in combination with clay), metals (including aluminium, nickel and alloys thereof), oxides (including aluminium oxides, silicon oxides), resins (including epoxyphenolic resins and ionomeric resins such as Surlyn®, trademark of DuPont), lacquers and enamels.

It is considered that one advantage of the present device is its relative simplicity and low cost to manufacture in addition to the ease of operability in terms of the minimum number of individual components or parts required for the storage and/or administration of the inhalable liquid. For example, the elongated body of the device may be formed as a single manufactured part. In one embodiment the internal shelf is an integrally formed component of the elongated body.

Embodiments of the device may require additional manufactured parts such as for example an air intake control means, an air filtering means and/or a removable end cap as described herein. Each manufactured part may be separately formed from the same or a different material. In one embodiment, the separately manufactured parts of the device are independently made from a material selected from the group consisting of a polymeric material, a metal (for example, aluminium, nickel) and a metal alloy (for example, stainless steel).

Polymers are particularly suited to large scale manufacturing of the present device and polymeric films described herein by injection moulding, blow moulding and extrusion processes. They may also be suitable for manufacturing the present device on a smaller scale by 3D printing techniques. Further, polymers may be recycled following disposal of the device.

Examples of polymers for use in making the present device and polymeric films described herein may include but are not limited to the following polymers and combinations (including co-extruded polymers) thereof: polyolefins such as polypropylene ('PP'), polyethylene (PE') including low density ('LDPE'), linear low density ('LLDPE') and high density polyethylene ('HDPE'), biaxially orientated polypropylene ('BOPP'), 4-methylpentene, polymethylpentene, polycyclomethylpentene; polymeric phthalates such as polyethylene naphthalates ('PEN'), polyethylene terephthalate ('PET') (also known as (PETE)), polyethylene terephthalate polyester 'PETP', polyethylene isophthalate ('PEI'), polybutylene terephthalate ('PBT'), polytrimethylene terephthalate ('PTT'), polycyclohexylenedimethylene terephthalate ('PCT'); fluorinated polymers including polymers fluorinated after manufacture (e.g. fluorination post-moulding), fluorinated ethylene-propylene, chlorotrifluoroethylene ('Kel-F'), polytetrafluoroethylene ('PTFE'); polyesters including cellulose acetate, polyoxymethylene ('POM') and polyesters containing a terephthalate ester group including co-polymers such polyethylene terephthalate glycol co-polyester ('PETG'), polycyclohexylenedimethylene terephthalate glycol modified ('PCTG') and polycyclohexylenedimethylene terephthalate/isophthalic acid ('PCTA'); nylons including amorphous nylon; polyvinyls including polyvinyl alcohol ('PVA') and ethylene vinyl alcohol ('EVOH'); polysulfones including polyethersulf one ('PES'); and natural polymers including starch, cellulose and proteins. Suitable polymers may also include polymers with a moisture vapor transmission rate ('MVTR', also known as water vapor transmission rate 'WVTR') of less than 100 g/m$^2$/24 h, preferably less than 50 g/m$^2$/24 h.

Accordingly, in one embodiment the device is made from one or more polymers wherein the device further comprises an optional internal lining or coating with one or more material(s) selected from the group consisting polymers (including homopolymers and heteropolymers (also known as co-polymers) and combinations thereof including co-extruded polymers), composites (including nanocomposites such as polymers in combination with clay), metals (including aluminium, nickel and alloys thereof), oxides (including aluminium oxides, silicon oxides), spray coatings, resins (including epoxyphenolic resins and ionomeric resins such as Surlyn®, trademark of DuPont), lacquers and enamels.

In one embodiment the polymer is selected from a polyolefin, a polymeric phthalate, a fluorinated polymer, a polyester, a nylon, a polyvinyl, a polysulfone, a natural polymer and combinations, including co-extruded polymers thereof. In one embodiment the polymer has a MVTR of less than 100 g/m$^2$/24 h, preferably less than 50 g/m$^2$/24 h. In one embodiment the polyolefin is selected from the group consisting of PP, PE, LDPE, LLDPE, HDPE, 4-methylpentene, polymethylpentene polycyclomethylpentene and combinations, including co-extruded polymers, thereof. In one embodiment the polymeric phthalate is selected from the group consisting of PEN, PET, PETP, PEI, PBT, PTT, PCT and combinations, including co-extruded polymers thereof such as BOPP. In one embodiment the fluorinated polymer is selected from Kel-F, PTFE and combinations, including co-extruded polymers thereof. In one embodiment the polyester is selected from the group consisting of cellulose acetate, POM and polyesters containing a terephthalate ester group including PETG, PCTG, PCTA and combinations, including co-extruded polymers, thereof. In one embodiment the nylon is an amorphous nylon. In one embodiment the polyvinyl is selected from PVA, EVOH and combinations, including co-extruded polymers, thereof. In one embodiment the polysulfone is PES. In one embodiment the natural polymer is selected from the group consisting of starch, cellulose, proteins and combinations, including co-extruded polymers, thereof.

In one embodiment the device is made from a single polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In another embodiment the device is made from two or more polymers selected from the group consisting of PP, PE, LDPE, LLDPE, HDPE, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In one embodiment, the device is made from a polymer selected from the group consisting of HDPE, PET and combinations thereof. In one embodiment the device comprises PET.

The elongated body of the device may generally adopt the same cross-sectional shape along its length. In one embodiment the cross-sectional shape of the elongated body is selected from the group consisting of circular, semi-circular, elliptical, semi-elliptical, oval, ovoidal, square, rectangular, trapezoidal, triangular and combinations thereof. Shapes having square corners may also be replaced with rounded corners, for example, a rectangle having a square corner replaced by a rounded one may be referred to as a rounded rectangular shape. In one embodiment the cross-sectional shape of the elongated body is selected from cylindrical, rectangular, rounded rectangular, trapezoidal and rounded trapezoidal. In one embodiment the cross-sectional shape of the elongated body is selected from cylindrical, rectangular, rounded rectangular, trapezoidal and rounded trapezoidal, with cylindrical being particularly preferred.

In one embodiment the base end is integrally formed with the elongated body. In another embodiment the base end comprises a removable end cap or is an adjustable end cap cover such as a rotatable end cap cover, a slidable or flip cover.

The cross-sectional shape of the mouthpiece end may be the same or different to the rest of the elongated body. In one embodiment, the mouthpiece is tapered towards the mouthpiece hole. In a preferred embodiment the cross-sectional shape of the mouthpiece hole is adapted to fit a conventional aerosol or nebuliser face mask.

Figure 4A:
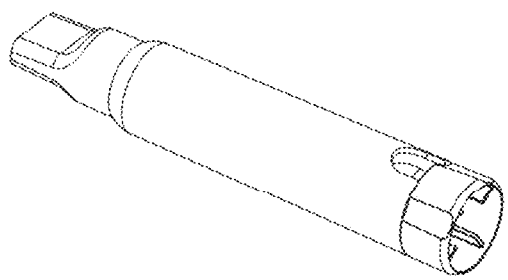
FIG. 4 shows an inhaler device according to an embodiment of the invention (FIG. 4A) and an enlarged view of the air intake control means located at the base end in the form of an adjustable rotatable cover (FIG. 4B).
FIG. 4C is an enlarged view of the circled portion of FIG. 4B.
Figure 4B:
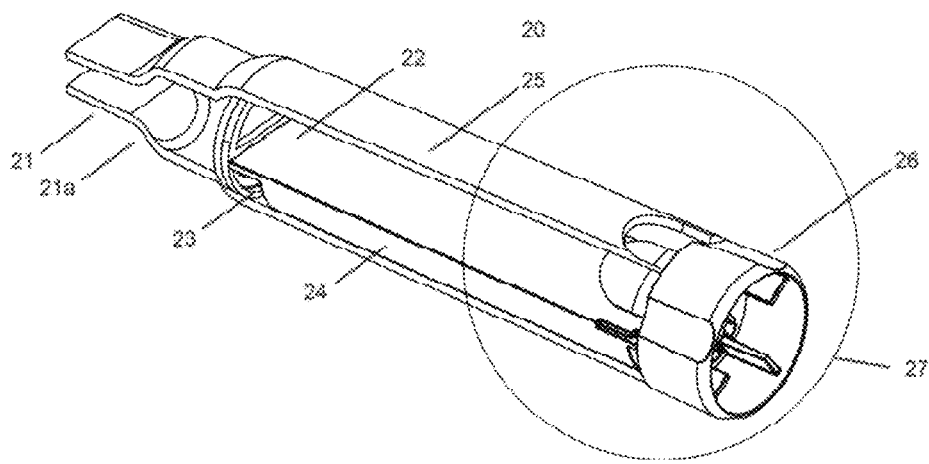
Figure 4C:
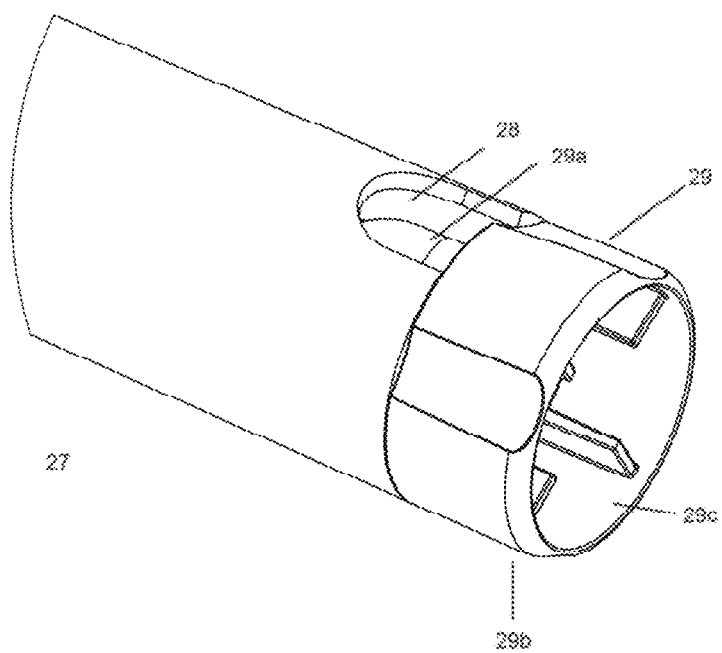

As the inhalable liquid may be self-administered by a patient using the device, the device may optionally comprise a lanyard and a point for attachment thereto for placement around the patient's wrist or neck. Accordingly, in one embodiment the device comprises a lanyard and a point for attachment thereto.

Example 1

FIG. 1 shows the prior art Green Whistle™ inhaler device (1) (Medical Developments International Limited) which is currently used in Australia for the delivery of Penthrox®/™ (methoxyflurane) as an analgesic (1.5 mL or 3 mL, storage brown glass vial container with screw cap). When required for use, the delivery dose of methoxyflurane is poured into the base end (3) of the device. After the dose is poured into the base end for delivery onto the evaporative means (not shown), the methoxyflurane evaporates so that the patient can self-administer the analgesic by inhaling the air/vapor mix through the mouthpiece (2). Provided that the patient continues to breathe through the mouthpiece, any exhaled air/vapor mix will exit the device via the externally fitted chamber containing activated carbon 'AC-chamber' (4).

Example 2

FIG. 2A shows an inhaler device (5) according to an embodiment of the invention. The device also comprises an internally stored passive evaporation support material in the air intake chamber which, although not shown, will be understood to be present for receiving the inhalable liquid and delivery of the air/vapor mix upon inhalation by the patient. The device comprises a mouthpiece end (6) a base end (7) which is integrally formed with the elongated body and comprises an air outlet hole (9). Two air inlet holes (8) are provided with one inlet hole being the same hole as liquid inlet hole (10). An air intake control means in the form of a flap cover comprising vents (11) is shown in its closed position covering air inlet hole (8)/liquid inlet hole (10). A cross-sectional view of the device along line A-A is shown in FIG. 2B to illustrate some of the internal features of the device such as the mouthpiece chamber (12), the air intake chamber (13), the air exit chamber (14), the air filtering means in the form of a cartridge (15) comprising end vents (15*a*) and (15*b*) and an internal shelf (16) to which it is attached. FIGS. 3A, 3B and 3C when viewed together, show an exploded view of the device to better illustrate some of its components. The outer shell portion of the elongated body that forms the walls and roof of the air intake chamber (13) and the top portion of the mouthpiece end comprising the mouthpiece chamber are shown in FIG. 3A. The flap cover is shown in an open position (17) as would enable the liquid to be poured from an external liquid storage container into the air intake chamber and onto the passive evaporation support material contained therein. The outer shell portion of the elongated body that forms the walls and the floor of the air exit chamber (14) and the bottom portion of the mouthpiece end comprising the mouthpiece chamber is shown in FIG. 3C. As shown in FIG. 3B, the internal shelf (16) to which the cartridge is attached also comprises a protrusion (16*a*). The protrusion is adapted for interlocking with a receiving portion in the valve holder (19) to hold the two-way valve (18) in place between the air intake chamber/mouthpiece chamber and the mouthpiece chamber/air exit chamber. The two-way valve is made from a flexible and air/vapor impermeable polymeric material such as PET.

Example 3

FIG. 4A shows an inhaler device (20) according to an embodiment of the invention. The device also comprises an internally stored passive evaporation support material in the air intake chamber which, although not shown, will be understood to be present for receiving the inhalable liquid and delivery of the air/vapor mix upon inhalation by the patient. The mouthpiece chamber (21a) in the mouthpiece end (21) is separated from the air intake chamber (22) and air exit chamber (23) by a two-way valve arrangement attached to the internal shelf (25). The air exit chamber comprises an air filtering means (24). The device also comprises an air intake control means located at the base end (26) of the elongated body in the form of a rotatable end cap cover (27). FIG. 4C shows an enlarged view of the adjustable rotatable end cap cover to better illustrate its components including the air inlet cover (29a) which is attached to or integrally formed with a rotatable base (29). The rotatable base may optionally comprise grips (29b) to assist with rotating the base. The air intake may be controlled by rotating the base to adjust the portion of the air inlet cover that covers the air inlet hole (28), which in this particular example, also functions as the liquid inlet hole. The rotatable base may also optionally comprise cap removal lugs (29c) to assist with removing screw caps from liquid storage vials. The rotatable base may be detachably fastened to the base end of the elongated body by a screw thread arrangement or a snap-fit joint arrangement (not shown).

Example 4

Figure 5A:
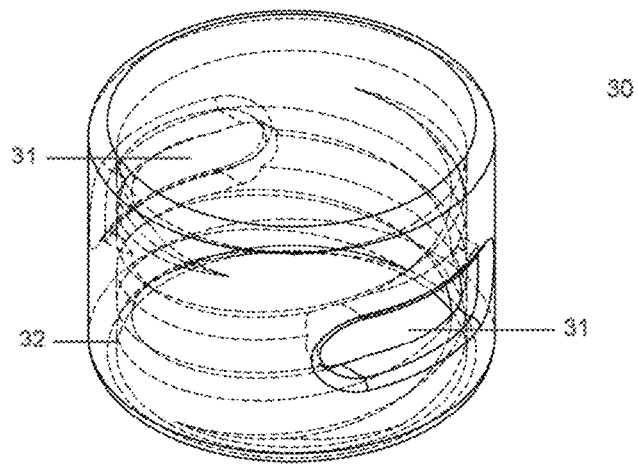
FIG. 5 shows a perspective view of an air intake control means according to an embodiment of the invention in the form of an adjustable sleeve cover comprising two air inlet holes (FIG. 5A) and another air intake control means according to an alternative embodiment of the invention in the form of an adjustable screw cap cover comprising two air inlet holes from a first side view (FIG. 5B) and a second side view (FIG. 5C).

FIG. 5A shows a perspective view of an air intake control means according to an embodiment of the invention in the form of an adjustable sleeve cover (30) comprising two air inlet holes (31). The adjustable sleeve cover is rotatably fastened to the elongated body by a screw thread arrangement (32).

Figure 5B:
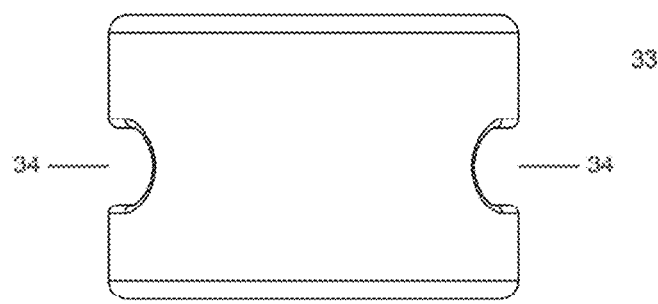
Figure 5C:
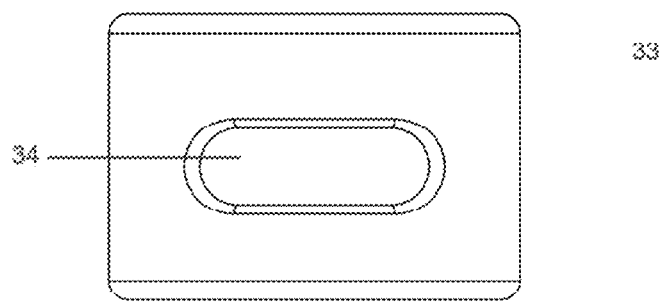

An air intake control means according to an alternative embodiment of the invention in the form of an adjustable screw cap cover (33) comprising two air inlet holes (34) is also shown in FIGS. 5B and 5C from a first side view and a second side view respectively. The adjustable screw cap cover is rotatably fastened to the base end of the elongated body by a screw thread arrangement.

The screw thread arrangements of the adjustable sleeve cover (30) and adjustable screw cap cover (33) may be a single screw thread arrangement or alternatively may be a double-screw thread arrangement. An advantage of a double-screw thread arrangement is to facilitate opening by minimising the number of rotations.

Example 5

Figure 6A:
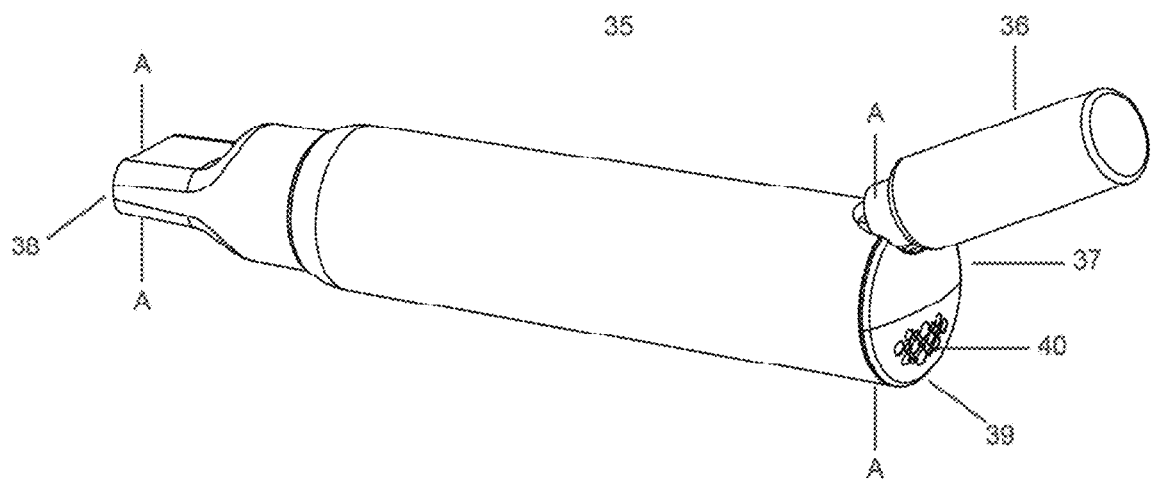
FIG. 6 shows an inhaler device according to an embodiment of the invention (FIG. 6A) and a cross-sectional view of the device along line A-A (FIG. 6B).
Figure 6B:
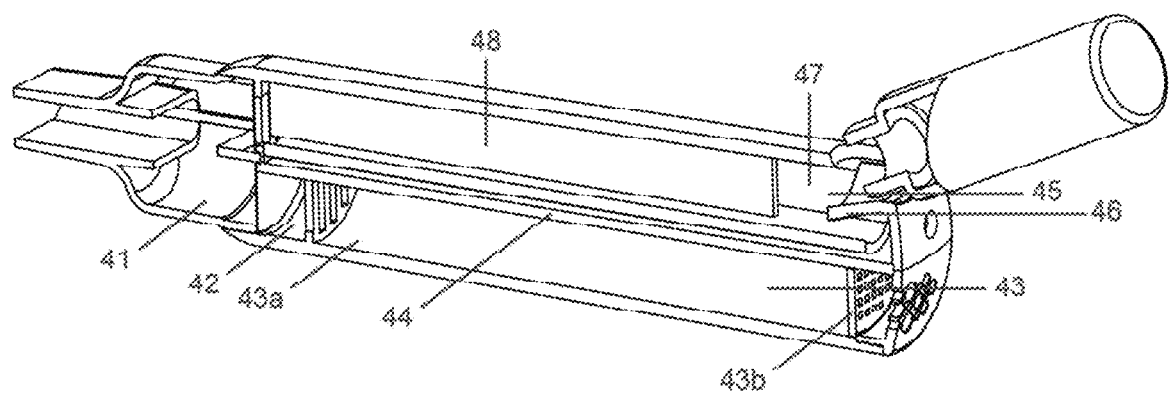
Figure 7A:
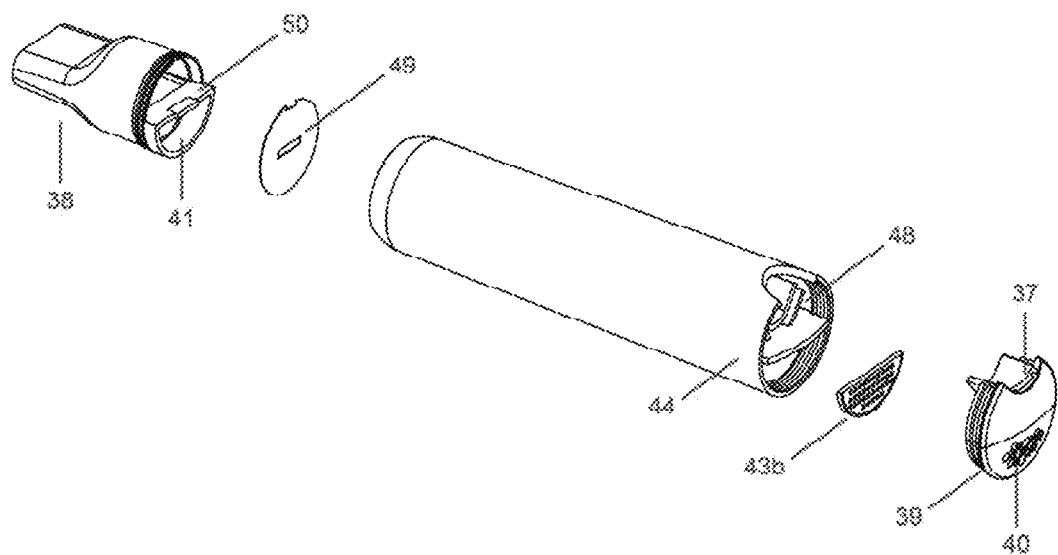
FIG. 7 shows an exploded view of the inhaler device of FIG. 6 from one perspective (FIG. 7A) and an alternative perspective (FIG. 7B) to better illustrate its components.
Figure 7B:
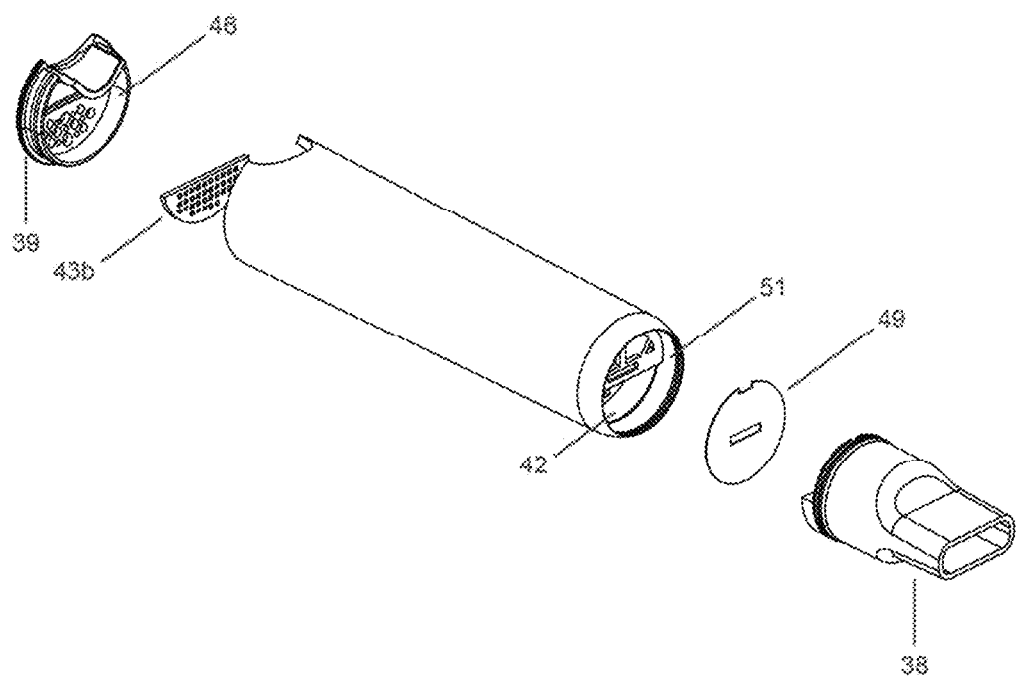

FIG. 6A shows an inhaler device (35) according to an embodiment of the invention. Liquid storage vial (36) is shown in the device loading position whereby the inhalable liquid contents are poured into the liquid inlet hole (37). In this example, the liquid inlet hole also functions as the air inlet hole. Also shown, are the mouthpiece end (38) and the base end in the form of a removable cap (39) with air outlet holes (40). FIG. 6B shows a cross-sectional view of the device along line A-A to illustrate some of the internal features of the device such as the mouthpiece chamber (41), the air intake chamber (45), the air exit chamber (42), the air filtering means in the form of a cartridge (43) comprising end vents (43a) and (43b) and an internal shelf (44) to which it is attached. Also shown is the liquid inlet guide (46) to assist with depositing the poured liquid onto the passive evaporation support material (47). The passive evaporation support material is positioned within the air intake chamber in a V-shape being held in place by a positioning means (48) in the form of a V-shape support integrally formed with the internal shelf together with an optional partitioning wall extending from the roof of the air intake chamber. An exploded view of the device from a first perspective and the reverse orientation are shown in FIGS. 7A and 7B to better illustrate the disassembled components including the two-way valve (49) and the protrusion (50) adapted for interlocking with a receiving portion in the internal shelf (51) to hold the valve in place between the air intake chamber/ mouthpiece chamber and the mouthpiece chamber/air exit chamber. The two-way valve is made from a flexible and air/vapor impermeable polymeric material such as PET.

Example 6

Figure 8A:
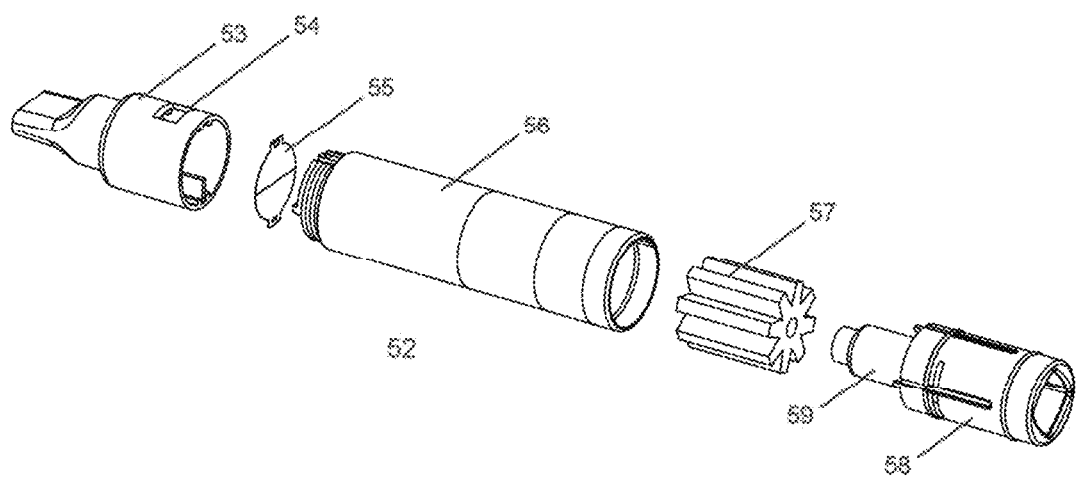
FIG. 8 shows an exploded view of an inhaler device according to an embodiment of the invention (FIG. 8A) and another embodiment further comprising an air filtering means (FIG. 8B). A top view (FIG. 8C) and perspective view (FIG. 8D) of a passive evaporation support material according to an embodiment of the invention and as shown in the devices of FIGS. 8A and 8B A is also provided.

FIG. 8A shows an exploded view of an inhaler device (52) according to an embodiment of the invention. The air exit chamber (not shown) is located in mouthpiece end (53) and comprises an air outlet hole (54). A one-way valve (55) is positioned between the mouthpiece chamber and the portion of the elongated body comprising the air intake chamber (56), the passive evaporation support material (57) and the storage chamber (58) shown with an inhalable liquid storage vial (59) in situ.

Example 7

Figure 8B:
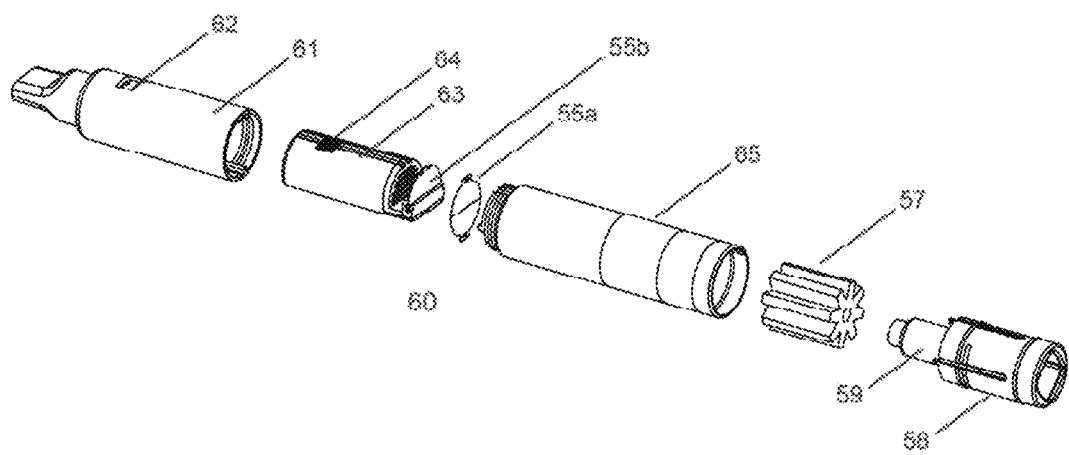

FIG. 8B shows an exploded view of an inhaler device (60) according to an embodiment of the invention. In contrast to the device of Example 6, the air exit chamber comprising an air filtering means (63) is located within the mouthpiece end (61). To accommodate the air exit chamber, the mouthpiece end is comparatively longer than the mouthpiece end in the device of Example 6. The air exit chamber comprises an air outlet hole (62) to align with an air outlet hole (64) in the air filtering means. A one-way valve (55a) is positioned between the mouthpiece chamber and the portion of the elongated body comprising the air intake chamber (65), the passive evaporation support material (57) and the storage chamber (58) shown with an inhalable liquid storage vial (59) in situ. Another one-way valve (55b) is positioned between the mouthpiece chamber and the entrance to the air exit chamber.

Example 8

Figure 8C:
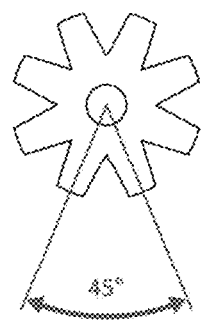
Figure 8D:
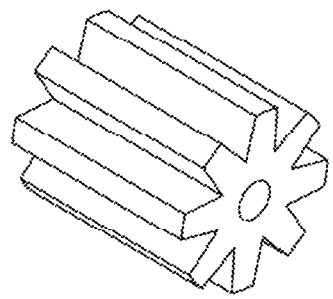

FIGS. 8C and 8D show a top view and perspective view respective of a passive evaporation support material (57) according to an embodiment of the invention. The passive evaporation support material comprises three or more radial arms extending from a central portion to an internal surface of the vapor chamber to form three or more longitudinal conduits.

Example 9

Figure 9A:
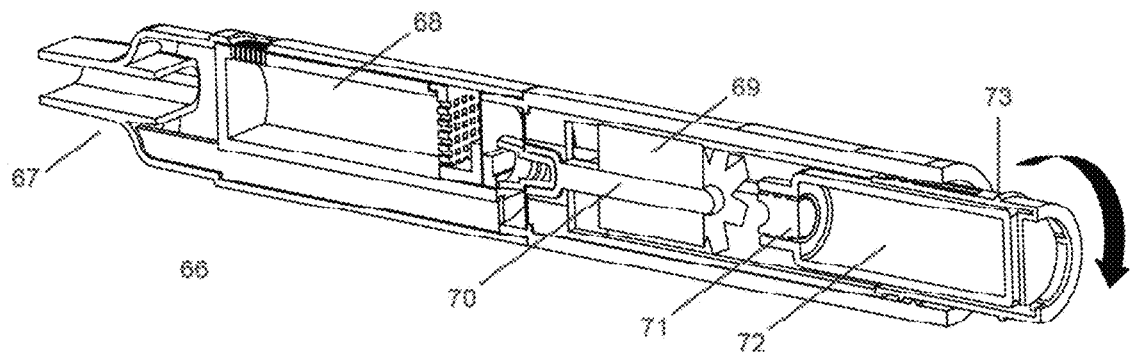
FIG. 9 shows a cross-sectional view of an inhaler device according to an embodiment of the invention to illustrate the device activation process. A liquid stored in a liquid storage container may be released onto a passive evaporation support material by activating a storage chamber in which the liquid storage container may be placed or stored (FIG. 9A). Activation of the storage chamber causes the liquid storage container to engage with a staving means (FIG. 9B) which pushes the seal of the liquid storage container into the container to release the liquid contents onto the passive evaporation support material (FIG. 9C).
Figure 9B:
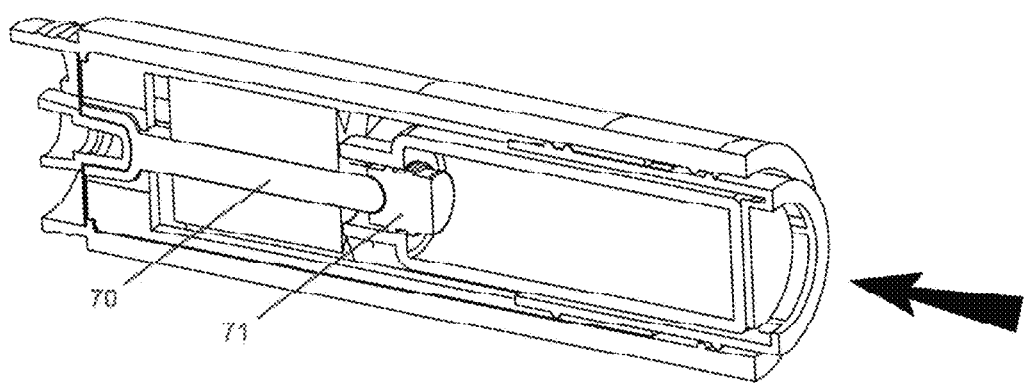
Figure 9C:
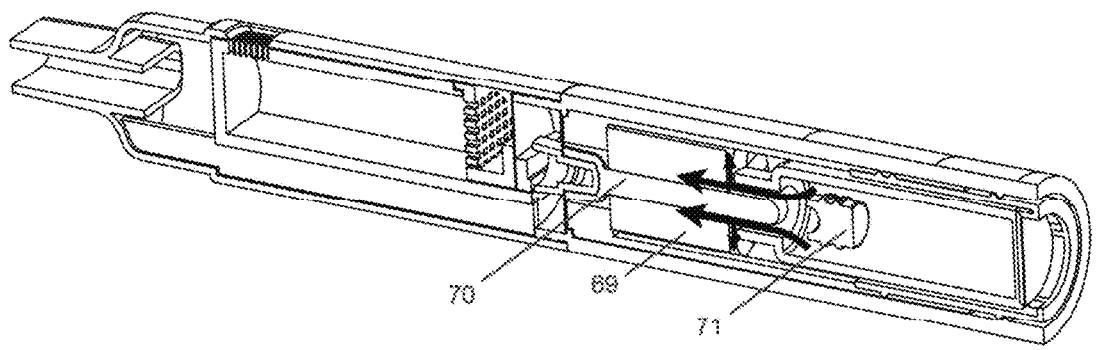

FIG. 9A shows a cross-sectional view of an inhaler device (66) according to an embodiment of the invention to illustrate the device activation process. An inhalable liquid stored in a liquid storage container (72) located in the storage chamber may be released onto a passive evaporation support material (69) by activating a container holder (73) in which the liquid storage container is held. Activation of the container holder by a turning and inwardly pushing action on the base end in the direction of the arrows, causes the liquid storage container to engage with a staving means (70)

as illustrated in FIG. 9B. The staving means then pushes the container seal (71) into the storage container to release the inhalable liquid onto the passive evaporation support material as shown in FIG. 9C.

Example 10

Figure 10A:
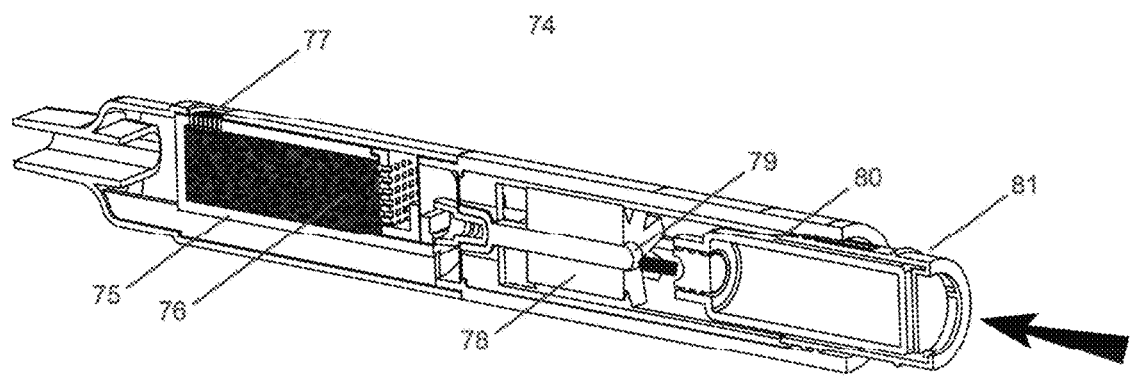
FIG. 10 shows a cross-sectional view of an inhaler device comprising a filtering means containing activated carbon granules according to an embodiment of the invention. The activation of a storage chamber in which a liquid storage container is placed or held by causing the liquid storage container to engage with a staving means to release the liquid onto the passive evaporation support material is shown (FIG. 10A). The direction of the air/vapor flow through the air intake chamber and mouthpiece chamber upon inhalation by the patient (FIG. 10B) and the direction of the air/vapor flow through the mouthpiece chamber and air filtering means in the air exit chamber upon exhalation by the patient (FIG. 10C) following release of the liquid onto the passive evaporation support material is illustrated by arrows.
Figure 10B:
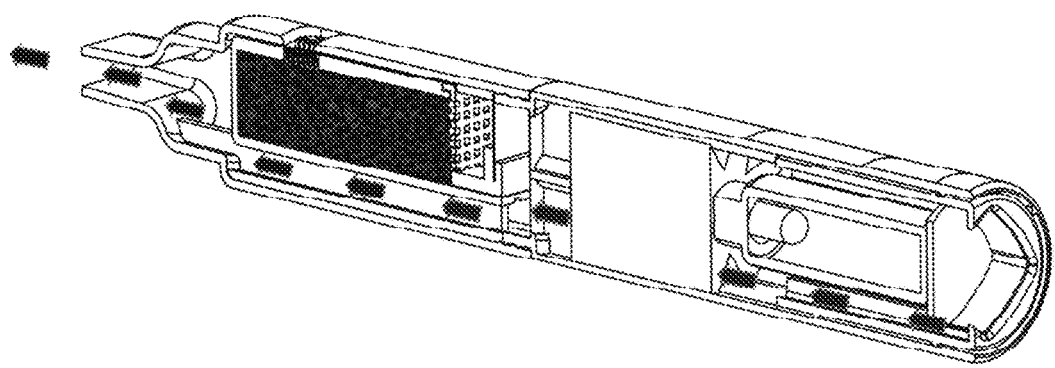
Figure 10C:
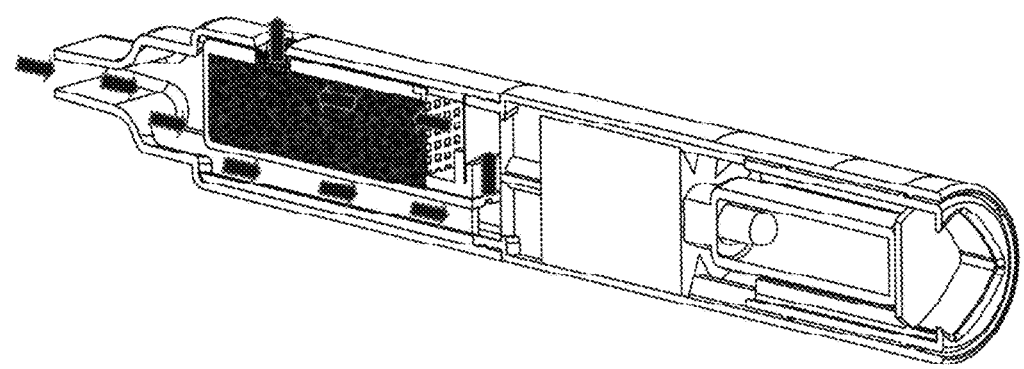

FIG. 10A shows a cross-sectional view of an inhaler device (74) according to an embodiment of the invention. The device comprises an air filtering means (75) containing activated carbon granules (76). The storage chamber comprising a container holder (81) in which a liquid storage container (80) is held is activated by pushing the base end in the direction of the arrows. The liquid storage container then engages with a staving means (79) to release the liquid onto the passive evaporation support material (79). The direction of the air/vapor flow upon inhalation by the patient following release of the liquid onto the passive evaporation support material (78) is illustrated in FIG. 10B. As shown by the arrows, the inhaled air/vapor flows through the storage chamber, air intake chamber, one-way valve and mouthpiece chamber for delivery to the patient. The direction of the air/vapor flow upon exhalation by the patient is illustrated in FIG. 100. As shown by the arrows, the exhaled air/vapor flows through the mouthpiece chamber, one-way valve, air filtering means in the air exit chamber and then leaves the device via the air outlet hole (77).

Example 11

Figure 11A:
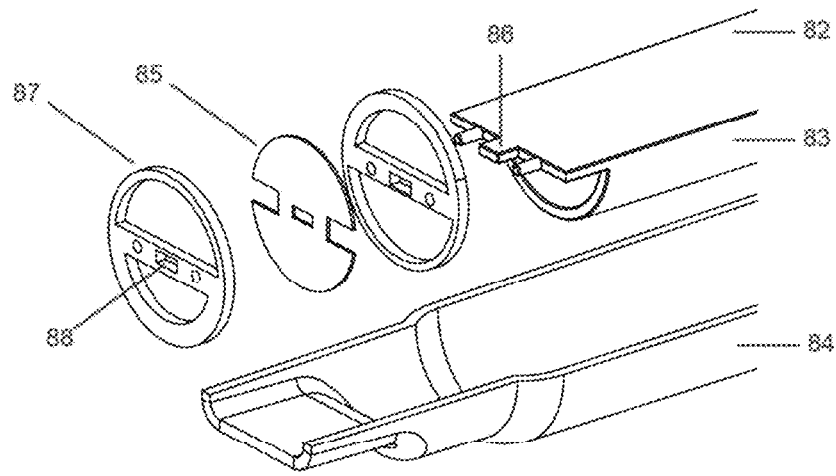
FIG. 11 shows a two-way valve according to an embodiment of the invention to illustrate its components (FIG. 11A), its assembly (FIG. 11B) and cross-sectional view of the two-way valve in a fully assembled device (FIG. 11C).
Figure 11B:
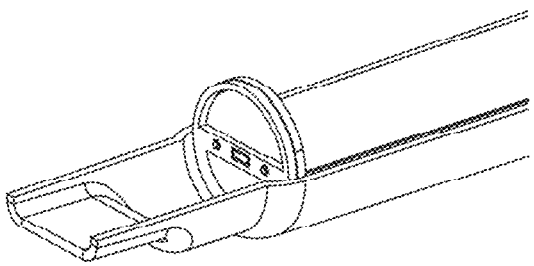
Figure 11C:
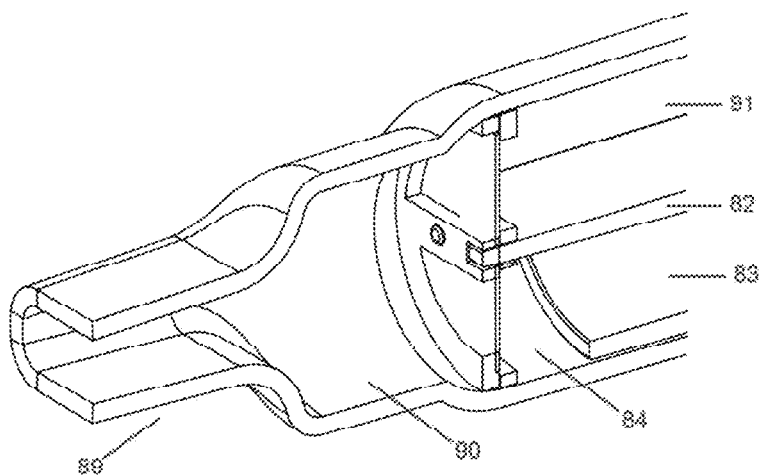

The components of a two-way valve according to an embodiment of the invention and their assembly within a device are shown in FIGS. 11A, 11B and 110. The internal shelf (82) to which an air filtering means in the form of a cartridge (83) is attached also comprises a protrusion (86). The protrusion is adapted for interlocking with a receiving portion (88) in the valve holder (87) and a receiving portion (86) in the two-way valve (85) to hold the two-way valve in place. FIG. 11B shows the assembled components of the two-way valve seated in the air exit chamber (84) which is formed in the bottom portion of the elongated body. FIG. 11C shows the assembled two-way valve in the fully constructed device located between the air intake chamber (91)/mouthpiece chamber (90) in the mouthpiece end (89) and the mouthpiece chamber (90)/air exit chamber (84). The two-way valve is made from a flexible and air/vapor impermeable polymeric material such as PET.

Example 12

Figure 12A:
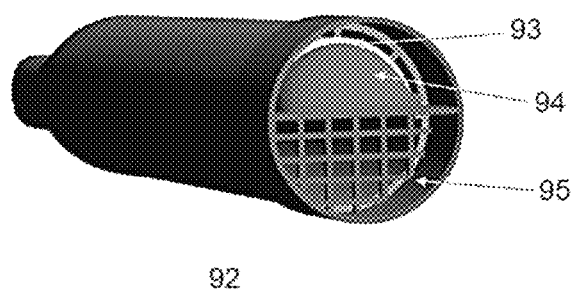
FIG. 12 shows an inhaler device according to an embodiment of the invention comprising a non-planar internal shelf from a rear perspective to illustrate its construction from the base end (FIGS. 12A and 12C) and an exploded view to illustrate its components (FIG. 12B).

FIG. 12A shows a rear perspective view of an inhaler device (92) according to an embodiment of the invention. To maximise the volume of the air exit chamber and the AC volume respectively, the internal shelf (93) is non-planar and comprises a recessed portion having a semi-circular cross-sectional profile which supports the passive evaporation support material. A large funneled guide (94) is provided to assist delivery of the poured liquid into the air intake chamber and onto the passive evaporation support material. An air outlet hole (95) is located in the base end.

Figure 12B:
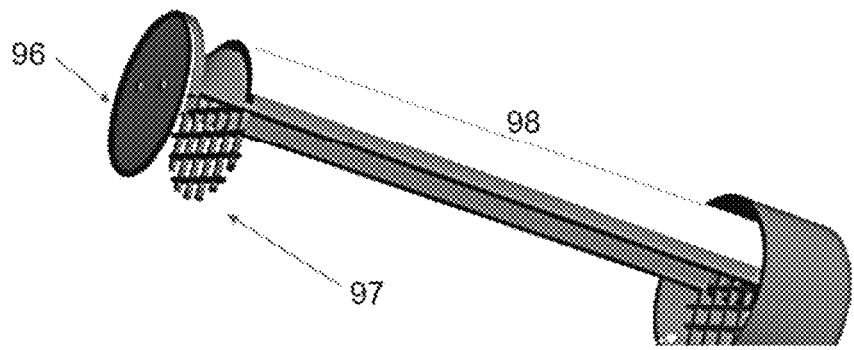

FIG. 12B shows a cut-away side view of the internal shelf of the device of FIG. 12A and related components including a two-way valve (96), mesh (97) to retain the AC within the air exit chamber and the passive evaporation support material (98) wrapped around the semi-circular recessed portion of the shelf.

Figure 12C:
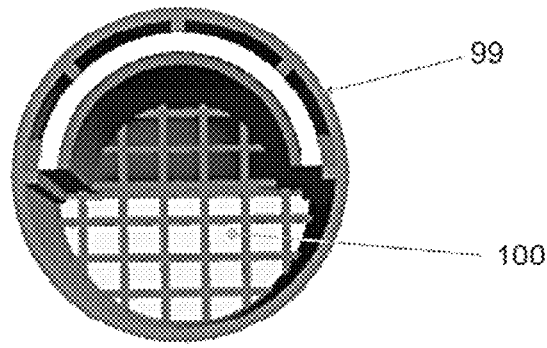

FIG. 12C shows a rear view of the inhaler device of FIG. 12A with optional ribs or pins or similar (99) to hold the passive evaporation support material in place and provide an air gap above it. The air exit chamber (100) of the device is capable of holding an approximate volume of 28 mL of AC which is equivalent to the volume of AC contained within the external AC chamber of the prior art Green Whistle inhaler of FIG. 1.

Example 13

Figure 13A:
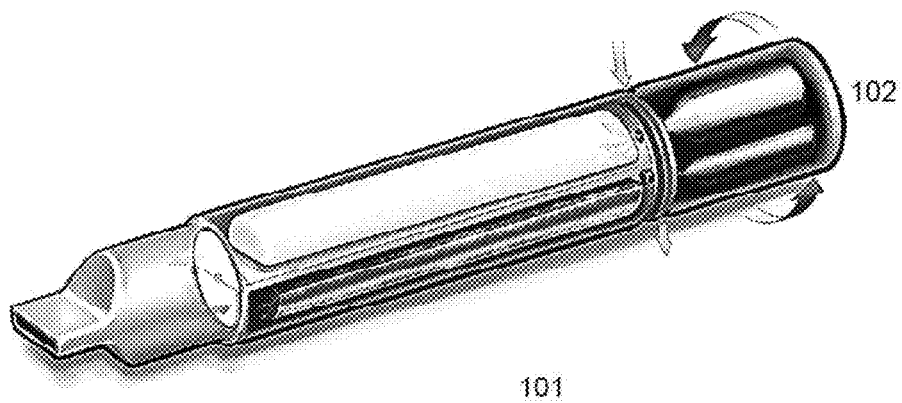
FIG. 13 shows an inhaler device according to an embodiment of the invention comprising a storage chamber movably connected to the base end of the elongated body for holding an inhalable liquid storage container in the form of an ampoule (FIG. 13A) and an enlarged view of the storage chamber comprising an unopened ampoule in a first position and movable to a second position to open the liquid storage container by snapping or similiar (FIG. 13B).

FIG. 13A shows a perspective side view of an inhaler device (101) according to an embodiment of the invention. The device comprises a storage chamber (102) movably connected to the base end of the elongated body of the device. The storage chamber is rotatable in the direction of the arrows shown.

Figure 13B:
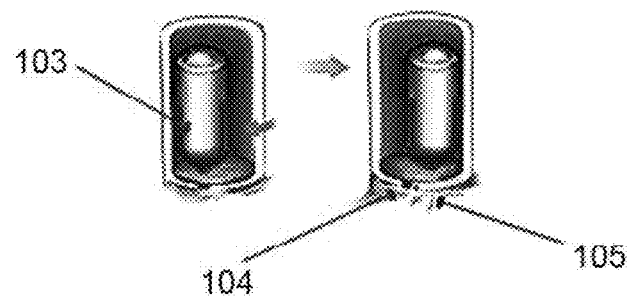

An enlarged view of the storage chamber is shown in FIG. 13B to further illustrate the inhalable liquid stored in a glass ampoule (103) which is moved when the storage chamber is rotated in the direction of the arrows shown, from a first position which holds the neck of the ampoule (104) into a second position (105) which causes the neck of the ampoule which is held in place to break to release the liquid into the air intake chamber and onto the passive evaporation support material.

Example 14

Figure 14A:
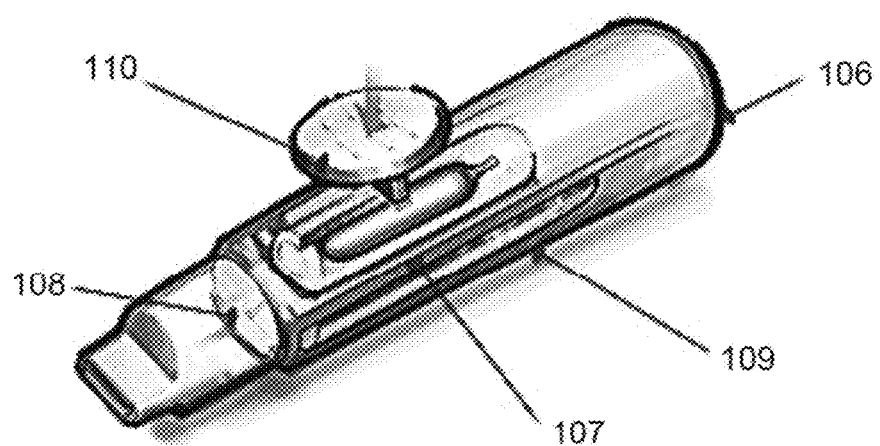
FIG. 14 shows an inhaler device according to an embodiment of the invention comprising a liquid storage container in the form of an ampoule located within the air intake chamber and positioned within the passive evaporative support material (FIG. 14B) to release the inhalable liquid onto the passive evaporation support material when opened by crushing or similar (FIG. 14A).

FIG. 14A shows a perspective view of an inhaler device (106) according to an embodiment of the invention. A liquid storage container in the form of an ampoule wrapped within the passive evaporation support material is positioned within the air intake chamber (107). A two-way valve (108) is provided to control the direction of the air/vapor flow through the air intake chamber and out of the air exit chamber comprising AC (109) when the user pushes down on the button (110) in the direction of the arrow shown to crush the ampoule to release the liquid from the ampoule.

Figure 14B:
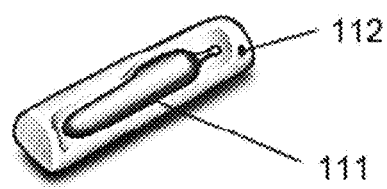

FIG. 14B shows an enlarged view of the ampoule (111) wrapped within the passive evaporation support material (112) the purpose of which is to prevent any fragments or shards resulting from the crushing of the ampoule from potentially entering the air/vapor flow.

Example 15

Figure 15A:
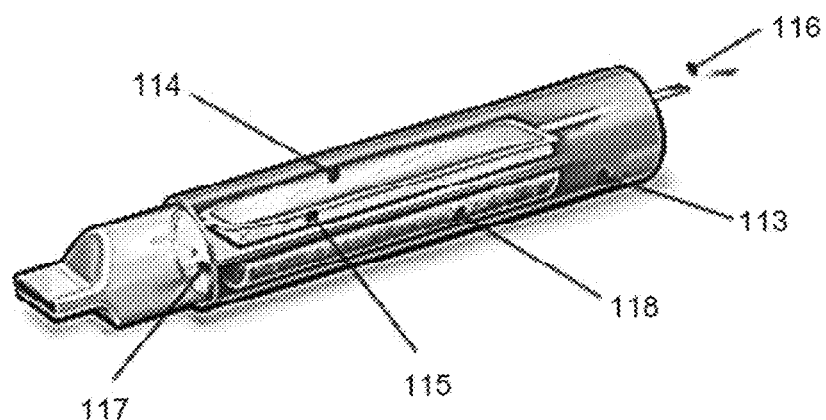
FIG. 15 shows an inhaler device according to an embodiment of the invention comprising a liquid storage container in the form of a vapor impermeable sachet or packet located within the air intake chamber and positioned above the passive evaporative support material (FIG. 15A) to release the inhalable liquid onto the passive evaporation support material when opened by ripping, unpeeling, pulling or similar (FIG. 15B).

FIG. 15A shows a perspective view of an inhaler device (113) according to an embodiment of the invention. A liquid storage container in the form of a vapor impermeable sachet or packet (114) is located within the air intake chamber and positioned above the passive evaporation support material (115). The liquid is released onto the passive evaporation support material by pulling a tab (116) to open the sachet in the direction of the arrow shown. A two-way valve (117) is provided to control the direction of the air/vapor flow through the air intake chamber and out of the air exit chamber comprising AC (118).

Figure 15B:
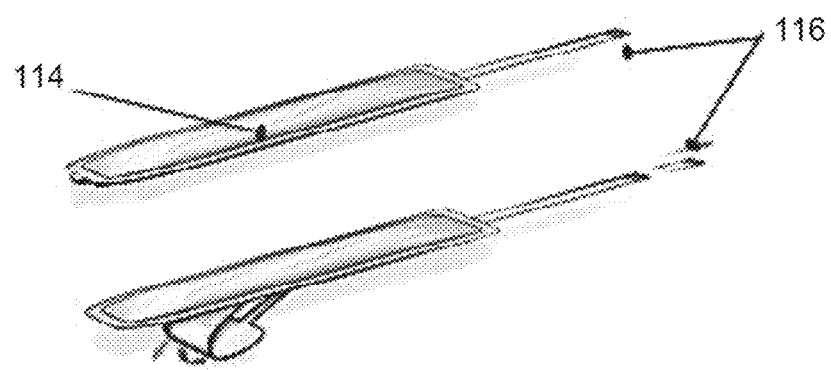

FIG. 15B provides an expanded view of the sachet (114) which is peeled opened in the direction of the arrows shown by pulling the tab (116).

Example 16

The ability of an inhaler device to delivery methoxyflurane may be tested using a breath simulator system such as a pulmonary waveform generator system.

The delivery of methoxyflurane (% concentration) by the Green Whistle device with the external AC chamber attached and a Prototype device (FIGS. 6-7) according to the invention was measured using a pulmonary waveform generator system. The Prototype device was manufactured as a rapid prototype using a HDPE equivalent material.

Both devices were tested as follows. The pulmonary waveform generator was set to "Adult" flow conditions (14 breaths per minute) and the concentration logging software and Datex Sensor commenced. For each test, methoxyflurane (3 mL) was poured into the device so that the polypropylene wick was pre-loaded with the methoxyflurane to be delivered and the mouthpiece end of the device then inserted into the opening of the pulmonary waveform generator. Concentration logging was commenced for the first minute for the first breaths concentration and then for the next 20 minutes for steady state testing.

Figure 16:
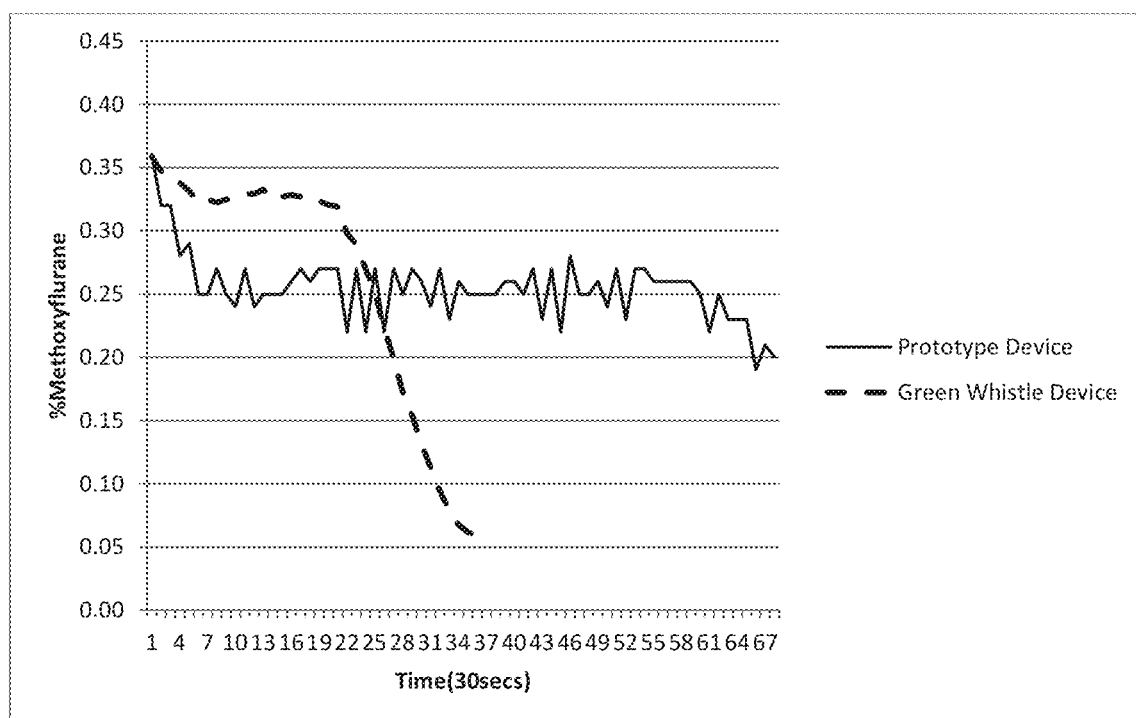
FIG. 16 shows the comparative concentrations of methoxyflurane delivered by a device (FIGS. 6-7) according to an embodiment of the invention and the prior art Green Whistle inhaler (FIG. 1).

The results are presented in FIG. 16. In both cases, the devices delivered methoxyflurane. However, while the initial first breaths concentration of methoxyflurane delivered by both devices starts off at the same level, the Prototype device was shown to maintain a steady state level over a longer period of time than the Green Whistle device. Accordingly, the Prototype device was shown to deliver a lower concentration of methoxyflurane for a longer duration. In contrast, the Green Whistle device was shown to deliver methoxyflurane at a higher steady state level for a shorter duration initially which was then followed by a rapid reduction below the steady state concentration of methoxyflurane achieved by the Prototype device.

Throughout this specification and the claims which follow, unless the context requires otherwise, the word "comprise" and variations thereof such as "comprises" and "comprising", will be understood to imply the inclusion of a stated integer or step or group of integers or steps but not to the exclusion of any other integer or step or group of integers or steps.

The reference in this specification to any prior publication or information derived from it, or to any matter which is known is not and should not be taken as an acknowledgement or admission or any form of suggestion that prior publication, or information derived from it, or known matter, forms part of the common general knowledge in the field of endeavour to which this specification relates.

The invention claimed is:

1. An inhaler device for the delivery of an inhalable liquid to a patient, said device comprising an elongated body wherein the elongated body comprises:
    (1) a base end;
    (2) a mouthpiece end comprising a mouthpiece chamber;
    (3) an air intake chamber comprising a passive evaporation support material for receiving the inhalable liquid from an external liquid storage container and at least one air inlet hole;
    (4) a liquid inlet hole for delivering the inhalable liquid from the external liquid storage container into the air intake chamber and onto the passive evaporation support material;
    (5) an air exit chamber comprising an air filter within the elongated body and comprising at least one air outlet hole; and
    (6) an internal shelf to partially divide the elongated body along its longitudinal axis from the base end and terminating at the mouthpiece chamber to form a floor of the air intake chamber and a roof of the air exit chamber.

2. The inhaler device according to claim 1 wherein the internal shelf is positioned within the elongated body to divide the internal volumes of the air intake chamber to the air exit chamber in a ratio selected from within a range of either 5:95 to 95:5 or 10:90 to 90:10.

3. The inhaler device according to claim 1 wherein the internal volume of the air intake chamber to the internal volume of the air exit chamber is in a ratio 50:50.

4. The inhaler device according to claim 1 further comprising a storage chamber for internally holding the liquid storage container wherein the storage chamber is adapted to deliver the inhalable liquid from the liquid storage container into the air intake chamber and onto the passive evaporation support material.

5. The inhaler device according to claim 1 further comprising a two-way valve abutted to the internal shelf at the mouthpiece end whereupon respiration by a patient through the mouthpiece end:
    (a) upon inhalation by the patient, opens the two-way valve between the air intake chamber and the mouthpiece chamber to deliver the evaporated liquid in the form of a vapor to the patient and closes the two-way valve between the air exit chamber and the mouthpiece chamber; and
    (b) upon exhalation by the patient, opens the two-way valve between the air exit chamber and the mouthpiece chamber to exhaust the expired air and closes the two-way valve between the air intake chamber and the mouthpiece chamber.

6. The inhaler device according to claim 1 further comprising a one-way valve between the air intake chamber and the mouthpiece chamber and/or a one-way valve between the mouthpiece chamber and the air exit chamber.

7. The inhaler device according to claim 1 wherein the air inlet hole further comprises an air intake control means.

8. The inhaler device according to claim 7 wherein the air intake control means is in the form of an adjustable cover located to adjustably cover the air inlet hole(s).

9. The inhaler device according to claim 8 wherein the adjustable cover is selected from the group consisting of a rotatable end cap cover located at the base end of the elongated body; a sleeve cover rotatably mounted around a circumference of the elongated body; a slideable cover; and a flap cover, the adjustable cover comprising one or more air inlet opening(s) to adjustably align with the air inlet opening(s) in the air intake chamber.

10. The inhaler device according to claim 1 wherein the passive evaporation support material is adapted to form at least two independent longitudinal airflow/vapor pathways though the air intake chamber.

11. The inhaler device according to claim 1 wherein the liquid storage container is selected from the group consisting of a vial, an ampoule or a vapor impermeable sachet or packet.

12. The inhaler device according to claim 1 wherein the inhalable liquid is methoxyflurane for use as an analgesic.

13. An inhaler device for the delivery of an inhalable liquid to a patient, said device comprising an elongated body wherein the elongated body comprises:
    (1) a base end;
    (2) a mouthpiece end comprising a mouthpiece chamber;
    (3) an air intake chamber comprising a passive evaporation support material for receiving the inhalable liquid from a liquid storage container and at least one air inlet hole;

(4) an air exit chamber comprising an air filter within the elongated body and comprising at least one air outlet hole; and (5) an internal shelf to partially divide the elongated body along its longitudinal axis from the base end and terminating at the mouthpiece chamber to form a floor of the air intake chamber and a roof of the air exit chamber;

wherein the liquid storage container is located within the air intake chamber and positioned to release the inhalable liquid onto the passive evaporation support material when opened.

14. The inhaler device according to claim 13 and further comprising a two-way valve abutted to the internal shelf at the mouthpiece end whereupon respiration by a patient through the mouthpiece end:

(a) upon inhalation by the patient, opens the two-way valve between the air intake chamber and the mouthpiece chamber to deliver the evaporated liquid in the form of a vapor to the patient and closes the two-way valve between the air exit chamber and the mouthpiece chamber; and (b) upon exhalation by the patient, opens the two-way valve between the air exit chamber and the mouthpiece chamber to exhaust the expired air and closes the two-way valve between the air intake chamber and the mouthpiece chamber.

15. The inhaler device according to claim 13 and further comprising a one-way valve between the air intake chamber and the mouthpiece chamber and/or a one-way valve between the mouthpiece chamber and the air exit chamber.

16. An inhaler device for the delivery of an inhalable liquid to a patient, said device comprising an elongated body wherein the elongated body comprises:

(1) a base end;

(2) a mouthpiece end comprising a mouthpiece chamber;

(3) an air intake chamber comprising a passive evaporation support material for receiving the inhalable liquid and at least one air inlet hole;

(4) a storage chamber for holding an inhalable liquid storage container wherein the storage chamber is adapted to deliver the inhalable liquid from the liquid storage container into the air intake chamber and onto the passive evaporation support material; and (5) an air exit chamber comprising an air filter and at least one air outlet hole;

wherein the storage chamber is located at the base end and the air intake chamber is located intermediate the storage chamber and the mouthpiece chamber and further wherein the air exit chamber is removably inserted within the mouthpiece chamber.

17. The inhaler device according to claim 16 wherein the storage chamber is moveable relative to the air intake chamber.

18. The inhaler device according to claim 16 wherein the storage chamber is movably connected to the base end of the elongated body.

19. The inhaler device according to claim 16 wherein the storage chamber comprises an unopened inhalable liquid storage container in a first position wherein the storage chamber is movable to a second position to open the liquid storage container to deliver the inhalable liquid from the liquid storage container into the air intake chamber and onto the passive evaporation support material.

20. The inhaler device according to claim 16 and further comprising a two-way valve abutted to the internal shelf at the mouthpiece end whereupon respiration by a patient through the mouthpiece end:

(a) upon inhalation by the patient, opens the two-way valve between the air intake chamber and the mouthpiece chamber to deliver the evaporated liquid in the form of a vapor to the patient and closes the two-way valve between the air exit chamber and the mouthpiece chamber; and (b) upon exhalation by the patient, opens the two-way valve between the air exit chamber and the mouthpiece chamber to exhaust the expired air and closes the two-way valve between the air intake chamber and the mouthpiece chamber.

* * * * *